(12) United States Patent
Burkart et al.

(10) Patent No.: US 8,653,283 B2
(45) Date of Patent: Feb. 18, 2014

(54) ANTICANCER AGENTS

(75) Inventors: Michael D. Burkart, San Diego, CA (US); James J. La Clair, San Diego, CA (US); MinJin Kang, San Diego, CA (US); Brian D. Jones, San Diego, CA (US); Alexander L. Mandel, San Diego, CA (US); Wei-Luen Yu, San Diego, CA (US); Justin C. Hammons, San Diego, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 13/263,141

(22) PCT Filed: Apr. 16, 2010

(86) PCT No.: PCT/US2010/031522
§ 371 (c)(1),
(2), (4) Date: Dec. 21, 2011

(87) PCT Pub. No.: WO2010/121226
PCT Pub. Date: Oct. 21, 2010

(65) Prior Publication Data
US 2012/0083527 A1  Apr. 5, 2012

Related U.S. Application Data

(60) Provisional application No. 61/170,211, filed on Apr. 17, 2009.

(51) Int. Cl.
*C07D 307/77* (2006.01)

(52) U.S. Cl.
USPC ............................................. 549/298

(58) Field of Classification Search
USPC ............................................. 549/298
See application file for complete search history.

(56) References Cited

PUBLICATIONS

Leslie et al. Chem Soc. Rev. 2008, 37, 1347-1360.*
Reymond et al. C. R. Chimie 11 (2008) 1447-1462.*
Dorwald F. A. Side Reactions in Organic Synthesis, 2005, Wiley: VCH, Weinheim p. IX of Preface p. 1-15.*
Venkatesh et al., J. Pharm. Sci. 89, 145-54 (2000).*
Jones et al. Organic Letters, 2010, 12(20), 4516-4519.*
Alexander, M.D. et al., "A Central Strategy for Converting Natural Products into Fluorescent Probes," ChemBioChem, 2006, pp. 409-416, vol. 7.
Dasgupta, T. et al., "Chemomodulation of Carcinogen Metabolising Enzymes, Antioxidant Profiles and Skin and Forestomach Papillomagenesis by *Spirulina platensis*," Molecular and Cellular Biochemistry, 2001, pp. 27-38, vol. 226.
Hughes, C.C. et al., "Ammosamides A and B Target Myosin," Angew. Chem, Int. Ed., 2009, pp. 728-732, vol. 48.
Kang, M. et al., "Isolation, Structure Elucidation, and Antitumor Activity of Spirohexenolides A and B," Journal of Organic Chemistry, 2009, pp. 9054-9061, vol. 74.
Leslie, B.J. et al., "Identification of the Cellular Targets of Bioactive Small Organic Molecules Using Affinity Reagents," Chemical Society Reviews, 2008, pp. 1347-1360, vol. 37.
Mishima, T. et al., "Inhibition of Tumor Invasion and Metastasis by Calcium Spirulam (Ca-SP), a Novel Sulfated Polysaccharide Derived from a Blue-Green Alga, *Spirulina platensis*," Clinical & Experimental Metastasis, Aug. 1998, pp. 541-550, vol. 16, No. 6.
Park, H-R. et al., "Relative and Absolute Configuration of Versipelostati n, a Down-Regulator of Molecular Chaperone GRP78 Expression," Organic Letters, 2007, pp. 1457-1460, vol. 9, No. 8.
PCT International Search Report and Written Opinion, PCT Application No. PCT/US2010/031522, Jan. 18, 2011, 13 pages.
Zhang, H. et al., "Elucidation of Kijanimicin Gene Cluster: Insights into the Biosynthesis of Spirotetronate Antibiotics and Nitrosugars," Journal of American Chemical Society, Nov. 28, 2007, pp. 14670-14683, vol. 129, No. 47.

* cited by examiner

*Primary Examiner* — Nizal Chandrakumar
(74) *Attorney, Agent, or Firm* — Fenwick & West LLP

(57) ABSTRACT

The present disclosure relates generally to compositions and methods for treating cancer. In some aspects, novel spirohexenolides and methods of using and producing them are described.

15 Claims, 17 Drawing Sheets

2a R=(S)-MTPA
2b R=(R)-MTPA

B

ANTICANCER AGENTS

CROSS REFERENCE TO RELATED APPLICATIONS

This application claims the benefit of U.S. Provisional Application No. 61/170,211, filed Apr. 17, 2009, the entire disclosure of which is hereby incorporated by reference in its entirety for all purposes.

FIELD

The present invention relates to novel compounds, herein designated spirohexenolides, which have diverse anticancer activity and other beneficial properties. The invention also relates to pharmaceutical compositions comprising such compounds and therapeutic methods involving administering such compounds and compositions.

BACKGROUND

The dominant therapeutic approaches that are currently employed to treat cancer include surgical removal of primary tumors, tumor irradiation, and parenteral application of antimitotic cytotoxic agents. The continued dominance of these long established therapies is mirrored by the lack of improvement in survival rates for most cancers. In addition to limited clinical success, devastating side effects accompany classic therapies. Both radiation- and cytotoxic-based therapies result in the destruction of rapidly dividing hematopoietic and intestinal epithelial cells leading to compromised immune function, anemia, and impaired nutrient absorption. Surgical intervention often results in a release of tumor cells into the circulation or lymph systems from which metastatic tumors can subsequently be established.

Metastasis still remains the main cause of death for most cancer patients. Despite years of research, the genetic mechanisms involved in the process are ill defined. Such information is of special importance in cancer prognosis given the uncertain course of the disease. The mechanisms which regulate the growth of the cancer cell are of particular relevance to the development of strategies for the treatment of metastatic cancer. Individual patients exhibit extreme variation in cancer progression. In some patients the cancer remains localized, whereas in other the cancer metastasizes quickly. Stromal-epithelial interactions (mediated through cytokine and other growth factors) with the extracellular matrix play a role in development of metastatic cancer.

Macrophage migration inhibitory factor (MIF) is a major mediator of innate immunity and inflammation (Calandra, Nat Rev Immunol, 3:791-800 (2003)) and represents a potential therapeutic target for multiple inflammatory, infectious, and autoimmune diseases, including cancer (Leech et al., Arthritis Rheum, 42:1601-1608 (1999); Morand, Intern Med J, 35:419-426 (2005); Bucala et al., Immunity, 26:281-285 (2007)). MIF is a homotrimeric multifunctional protein that could function as a cytokine, hormone, and/or enzyme. Three non-physiological substrates are reported for MIF tautomerase activity: the D-dopachrome methyl ester, phenyl pyruvic acid, and hydroxyphenyl pyruvic acid (Rosengren et al., FEBS Lett, 417:85-88 (1997); Sugimoto et al., Biochemistry, 38:3268-3279 (1999)). Although the link between the enzymatic activity of MIF and its biological function remains controversial, there is sufficient evidence to suggest that MIF's tautomerase activity and/or catalytic site modulates some of its proinflammatory function(s) (Dios et al., J Med Chem, 45:2410-2416 (2002); Swope et al., EMBO J, 17:3534-3541 (1998)). Therefore, blocking the enzymatic activity of MIF as a means of attenuating and/or neutralizing its cellular function(s) has emerged as a promising strategy to treat MIF-related diseases, including septic shock, rheumatoid arthritis, atherosclerosis, and multiple sclerosis.

MIF's 3D structure was resolved in 1996. Subsequent biochemical and mutagenesis studies have allowed the identification of the key residues involved in forming the catalytic site and in regulating MIF's tautomerase activity (Johnson et al., Biochemistry, 38:16024-16033 (1999)). Since that time, significant efforts have attempted to identify small-molecule modulators of MIF by targeting its tautomerase activity (Orita et al., Curr Pharm Des, 8:1297-1317 (2002)). The availability of X-ray structures of the MIF trimer and the tautomerase catalytic site has facilitated these efforts and has stimulated great interest in rationally developing structure-based inhibitors. The first MIF inhibitors were identified by testing different D-dopachrome derivatives or phenyl pyruvic acid analogs (Zhang et al., Bioorg Med Chem Lett, 9:3193-3198 (1999)). In the past decade, several classes of MIF inhibitors have been developed by introducing modifications on substrate analogs and by screening focused libraries of natural products (Orita et al., Curr Pharm Des, 8:1297-1317 (2002); Orita et al., J Med Chem, 44:540-547 (2001)). Several of these inhibitors were later shown to modulate MIF's biological activities (e.g., IS01 and OXIME11) in cellular models and in vivo (Al-Abed et al., J Biol Chem, 280:36541-36544 (2005); Dabideen et al., J Med Chem, 50:1993-1997 (2007)).

Because of the shortcomings of classic treatment regimens, there is a need in the art for improved anticancer therapies. One potential and underdeveloped therapeutic area includes MIF inhibitors.

SUMMARY

The present disclosure addresses long-felt needs in the field of medicine by providing novel compositions and methods for cancer treatment.

Briefly stated, the present disclosure provides methods and compositions for the inhibition of tumor growth. The present disclosure relates to novel spirohexenolides, biosynthetic methods for producing these spirohexenolides, and methods of treating cancer using the novel spirohexenolides.

The present disclosure provides for the compound of formula (I) or a pharmaceutically acceptable salt, metabolite, prodrug or stereoisomer thereof:

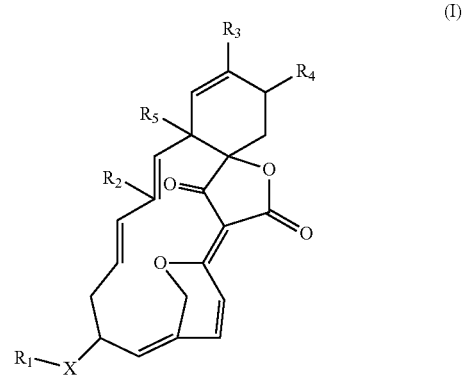

(I)

wherein X is a direct bond, —C—, —O—, —C(=O)—, —O—C(=O)—, —O—C(=O)—O—, —S—, or —C(=O)NH—;

$R_1$ is H, $C_1$-$C_6$ alkyl, $C_2$-$C_6$ alkenyl, $C_2$-$C_6$ alkynyl, $C_1$-$C_6$ alkoxy, —$CF_3$, aryl, heteroaryl, or a label;

$R_2$, $R_3$, $R_4$, and $R_5$ are independently H, $C_1$-$C_6$ alkyl, $C_2$-$C_6$ alkenyl, $C_2$-$C_6$ alkynyl, $C_1$-$C_6$ alkoxy, halo, —$CF_3$, —$OR_6$, —$C(O)R_6$, —$NHC(O)R_6$, —$C(O)OR_6$, —$OC(O)R_6$, —$NR_7R_8$, —$C(O)NR_7R_8$, —$NHR_6C(O)NR_7R_8$, or —$SO_2NR_7R_8$; and $R_6$, $R_7$, and $R_8$ are independently H, $C_1$-$C_6$ alkyl, $C_2$-$C_6$ alkenyl, $C_2$-$C_6$ alkynyl, $C_1$-$C_6$ alkoxy, halo, aryl, or heteroaryl, each being optionally substituted with one or more of the following substitutents: halo or $C_1$-$C_6$ alkyl.

In some aspects, the present disclosure provides for a compound having the structure of formula (II):

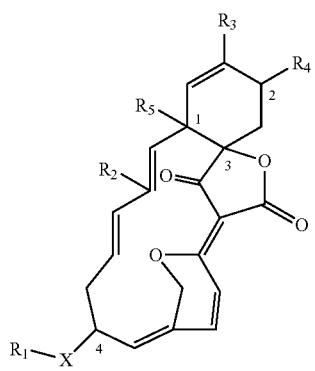

(II)

wherein carbon 1 is in the R configuration, S configuration, or a combination thereof.

In further aspects, carbon 2 as provided in formula (II) is in the R configuration, S configuration, or a combination thereof.

In further aspects, carbon 2 as provided in formula (II) is in the R configuration, S configuration, or a combination thereof.

In further aspects, carbon 2 as provided in formula (II) is in the R configuration, S configuration, or a combination thereof.

In certain aspects, the present disclosure provides for compounds having the structure and stereochemical configuration of formula (III):

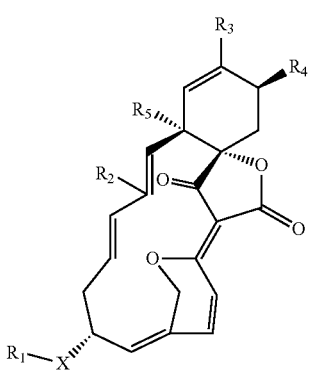

(III)

and pharmaceutically acceptable analogues, salts, prodrugs, metabolites.

In some aspects, the present disclosure provides for compounds having the structure of formula (I), w wherein $R_1$ is H or —$C(O)CH_3$.

In certain aspects, the present disclosure provides for compounds having the structure of formula (IV):

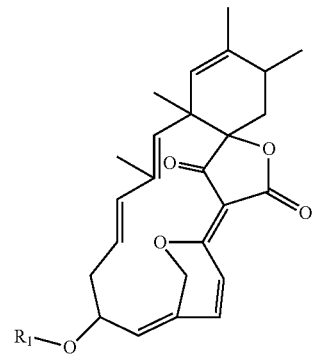

(IV)

In certain aspects, the present disclosure provides for compounds having the structure of formula (V):

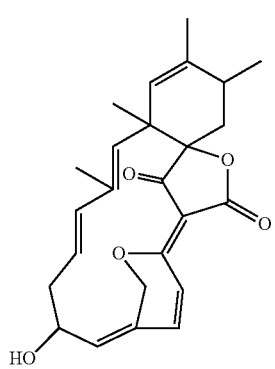

(V)

In further aspects, the present disclosure provides for compounds having the structure of formula (VI):

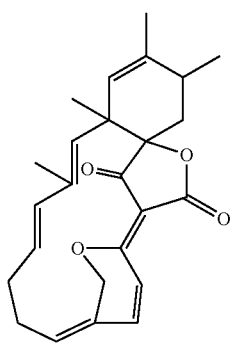

(VI)

In one aspect, the present disclosure provides for a compound referred to as spirohexenolide A, which has the structure and stereochemical configuration of formula (VII):

(VII)

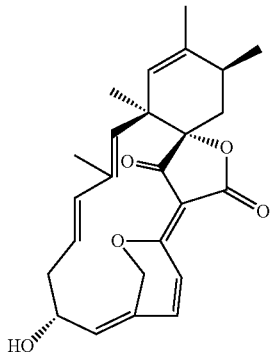

In one aspect, the present disclosure provides for a compound referred to as spirohexenolide B, which has the structure and stereochemical configuration of formula (VIII):

(VIII)

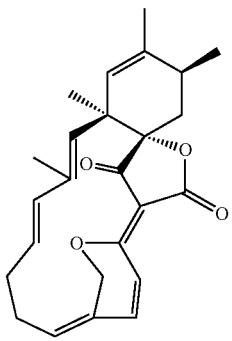

In certain aspects, the present disclosure provides for compounds optionally having a label at $R_1$. In further aspects, the label is an immunological label, a fluorescent label, a chemiluminescent label, a radioisotope label, an enzyme label, a particulate label, a colorimetric label, or an energy transfer agent. In further aspects, the label is α-methoxy-α-trifluoromethylphenylacetic acid (MTPA), fluorescent dye, affinity tag, soublizing group, or an immunoaffinity fluorescent (IAF) label.

In some aspects, the present disclosure provides for methods of screening for proteins that bind to the compounds of the present disclosure comprising exposing a cancerous tissue to a compound comprising a label and detecting the presence of the labeled compound.

In some aspects, the present disclosure provides for pharmaceutical compositions comprising a therapeutically effective amount of a compound of the present disclosure or a pharmaceutically acceptable salt, metabolite, prodrug or stereoisomer thereof, and a pharmaceutically acceptable excipient.

In one aspect, the present disclosure provides for pharmaceutical compositions comprising a therapeutically effective amount of a compound having the structure and stereochemical configuration of formula (IX):

(IX)

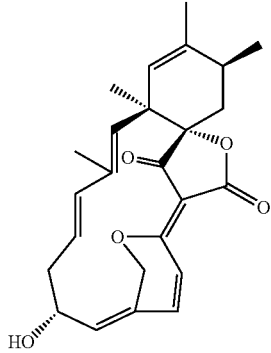

In some aspects, the present disclosure provides for methods of treating cancer, comprising administering a therapeutically effective amount of a compound of the present disclosure, or a pharmaceutically acceptable salt, metabolite, prodrug or stereoisomer thereof, to a subject in need of treatment.

In one aspect, the present disclosure provides for methods of treating cancer comprising administering the compound having the structure and stereochemical configuration of formula (X) or a pharmaceutically acceptable salt, metabolite, prodrug or stereoisomer thereof, to a subject in need of treatment:

(X)

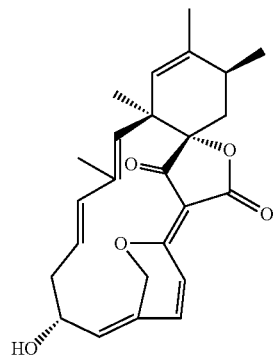

In some aspects, the present disclosure provides a process for preparing the compounds of the present disclosure, the process comprising culturing a microorganism having the identifying characteristics of *Streptomyces platensis* under suitable conditions, allowing the compound to accumulate in the culture medium, and isolating the compound from the culture medium. In certain aspects, the process further comprises the steps of inducing mutations in *Streptomyces platensis* microorganisms by exposing the microorganisms to a mutagen, selecting the resulting microorganisms having a desired trait, and culturing the selected organisms. In further aspects, the mutagen is ultraviolet irradiation, ionizing radiation, or a chemical mutagen. In yet further aspects, the desired characteristic is decreased contact inhibition. In certain aspects, the microorganism is strain MJ1A1 or MJ1A2 of *Streptomyces platensis*. In some aspects, the present disclosure provides for compounds prepared by the processes of the present disclosure.

DETAILED DESCRIPTION

Figure 1:
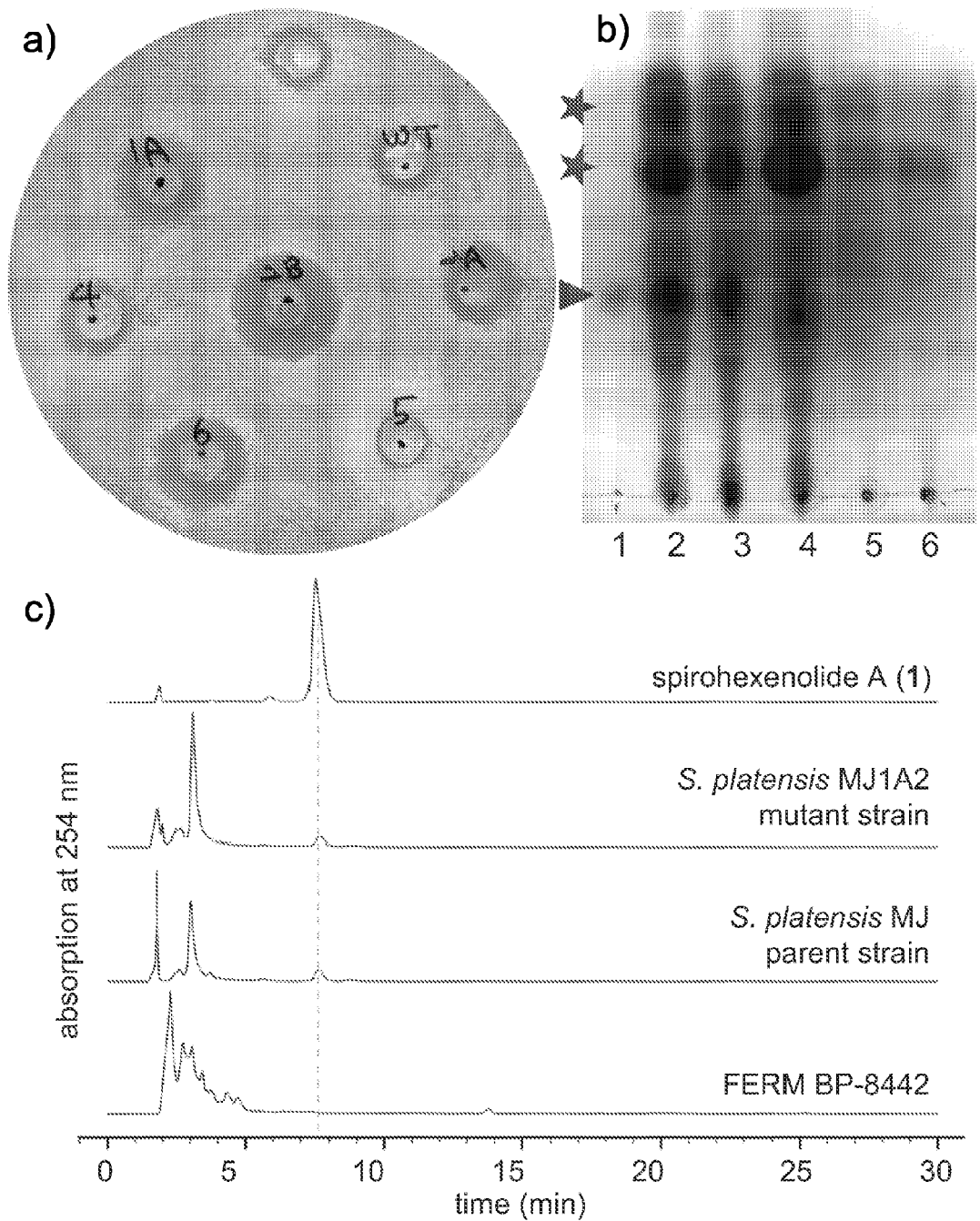
FIG. 1 shows the strategy for producing metabolite 1 from *Streptomyces platensis* strains MJ1A1 and MJ1A2. (a) Ultraviolet light mutagenesis (Pang et al., Antimicrob Agents Chemother, 48:575-588 (2004); Kieser et al., Practical *Streptomyces* Genetics, 102-103 (2000); Baltz, Antonie van Leeuwenhoek, 79:251-259 (2001)) provided mutants with an increased ability to inhibit the growth of *Bacillius subtilis* 6633 (A number of mutant screening approaches were evaluated at the onset of this program and an antibiotic assay using *B. subtilis* was eventually chosen. This assay was particularly relevant to the discovery of a spirotetronate natural product, as prior studies have shown Schindler et al., Eur Biochem, 39:591-600 (1973); Gary et al., J Bacteriol, 64:501-512 (1952); Sundaram et al., Biochim Biophys Acta, 192:355-357 (1969). An enhanced zone of growth inhibition was observed from mutant strains MJ1A, MJ2B, and MJ6 as compared to their parent strain (wt). (b) TLC analysis of extracts from *S. platensis* strains cultures. A direct comparison of crude extracts from these cultures indicates that metabolite 1 (lane 1) was enhanced in *S. platensis* strain MJ1A1 (lane 2) and strain MJ1A2 (lane 3), as compared to their parental strain (lane 4), a gray colony of *S. platensis* FERM BP-8442 (lane 5) or a white colony of *S. platensis* FERM BP-8442 (lane 6). An arrow denotes position of metabolite 1. The TLC observations were confirmed by preparative isolation, which after multiple repeats failed to return traces of 1 from cultures of the strains in lanes 5 and 6. (c) HPLC traces collected with UV detection at 254 nm confirmed the presence of 1 in both parent *S. platensis* MJ and mutant *S. platensis* MJ1A2 strains while not in *S. platensis* FERM BP-8442. The MIC of pure 1 against *Bacillus subtilis* was determined to be 12.25 µM (see the Experimental Section), therein supporting the viability of the screening procedure.

Briefly stated, the present disclosure provides methods and compositions for the inhibition of tumor growth. The present disclosure relates to novel spirohexenolides, biosynthetic methods for producing these spirohexenolides, and methods of treating cancer using the novel spirohexenolides.

The descriptions of various embodiments of the invention are presented for purposes of illustration, and are not intended to be exhaustive or to limit the invention to the forms disclosed. Persons skilled in the relevant art can appreciate that many modifications and variations are possible in light of the embodiment teachings. Accordingly, the disclosure is intended to be illustrative, but not limiting, of the scope of invention.

It must be noted that, as used in the specification, the singular forms "a," "an" and "the" include plural referents unless the context clearly dictates otherwise.

Any terms not directly defined herein shall be understood to have the meanings commonly associated with them as understood within the art of the invention. Certain terms are discussed herein to provide additional guidance to the practitioner in describing the compositions, devices, methods and the like of embodiments of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the invention herein.

Macrophage migration inhibitory factor (MIF) is a major mediator of innate immunity and inflammation and represents a potential therapeutic target for multiple inflammatory, infectious, and autoimmune diseases, including cancer. MIF is a homotrimeric multifunctional protein that could function as a cytokine, hormone, and/or enzyme. MIF was found to catalyze a tautomerization reaction (Rosengren, et al., Molecular Medicine 2:143-149, 1996), and although the most active substrate identified to date is the non-physiological D-isomer of dopachrome, the observation that MIF can catalyze a tautomerization reaction points to the possibility of developing inhibitors of MIF enzymatic activities as therapeutic MIF inhibitors. The present disclosure encompasses compounds and the use of compounds that are identified as MIF inhibitors. Also contemplated by the present disclosure are methods for screening compounds for the inhibition of MIF.

The present invention is related generally to a class of novel bioactive compounds having the structure of formula (I) and pharmaceutically acceptable analogues, salts, prodrugs, metabolites, and stereoisomers thereof (collectively referred to herein as "spirohexenolides")

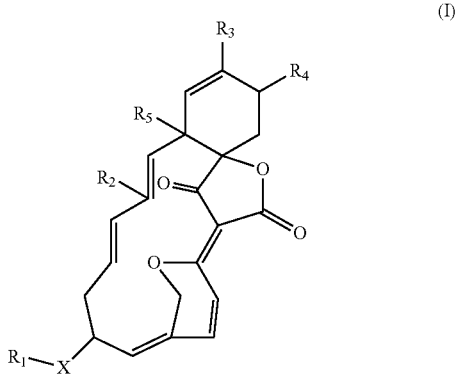

In certain aspects, the present disclosure provides for spirohexenolide A (1), spirohexenolide B (2), and pharmaceutically acceptable analogues, salts, prodrugs, metabolites, and stereoisomers thereof.

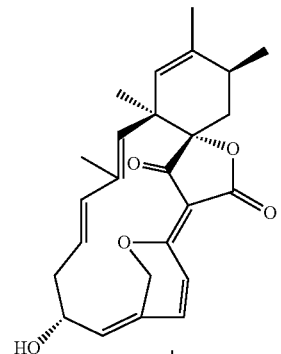

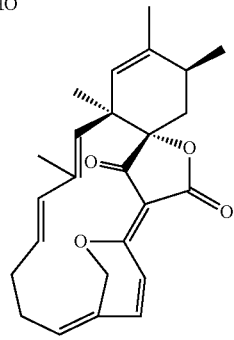

As described herein, spirohexenolide A was isolated from mutant strains of Streptomyces platensis that were developed using mutagenesis and clonal selection methods. Spirohexenolides have a novel structure, including a unique fused pyran and spirotetronic acid functionality, and have diverse anticancer, antibiotic, antihelminthic, antifungal and/or other beneficial properties. For example, spirohexenolide A has been shown to inhibit mitosis in colon cancer cells (HCT111), breast cancer cells (HeLa) and neuroblastoma cells (Neuro2a) by inhibiting the exit from anaphase. This mechanism of cell cycle inhibition differs from that of known natural products, giving rise to a new approach for treating cancer and/or other conditions.

Since its classification in 1956 (Backus et al., Appl Microbiol, 4:243-250 (1956)), Streptomyces platensis has demonstrated a remarkable ability to produce biologically active polyketides including the dorrigocins (Ju et al., J Am Chem Soc, 127:1622-1623 (2005); Kadam et al., J Antibiot (Tokyo), 47:875-880 (1994); Hochlowski et al., J Antibiot (Tokyo), 47:870-874 (1994); Karwowski et al., J Antibiot (Tokyo), 47:862-869 (1994)), the migrastatins (Woo et al., J Antibiot (Tokyo), 55:141-146 (2002); Gaul et al., J Am Chem Soc, 126:11326-11337 (2004); Njardarson et al., J Am Chem Soc, 126:1038-1040 (2004)), the pladienolides (Sakai et al., J Antibiot (Tokyo), 57:173-179 (2004); Mizui et al., J Antibiot (Tokyo), 57:188-196 (2004); Kotake et al., Nat Chem Biol, 3:570-575 (2007); Mandel et al., Bioorg Med Chem Lett, 17:5159-5164 (2007); Kanada et al., Angew Chem Int Ed Engl, 46:4350-4355 (2007); Kanada et al., Angew Chem Int Ed Engl, 46:8734 (2007); Asai et al., J Antibiot (Tokyo), 60:364-369 (2007); Skaanderup et al., Org Lett, 10:2821-2824 (2008)), leustroducsin B (Miyashita et al., J Org Chem, 73:5360-5370 (2008); Shimada et al., J Am Chem Soc, 125:4048-4049 (2003); Kohama et al., J Antibiot (Tokyo), 49:91-94 (1996)), TPU-0037 (Furumai et al., J Antibiot (Tokyo), 55:873-880 (2002)), platensimide A (Herath et al., Org Lett, 10:699-702 (2008)), and platensimycin (Wang et al., Nature, 441:358-361 (2006)). Many of these compounds, including the migrastatins and pladienolides, have demonstrated potent activity against tumor progression (Ju et al., Bioorg Med Chem Lett, 18:5951-5954 (2008); Metaferia et al., J Am Chem Soc, 129:2434-2435 (2007)), and an analog of pladienolide D, E7107, has recently entered clinical trials (Kotake et al., Nat Chem Biol, 3:570-575 (2007)).

Recently, genome sequencing studies suggest that the bacterial secondary metabolomes are far more complicated than previously recognized by evaluation of their natural product content (Li et al., BMC Bioinf, 10:185 (2009); Gulder et al., Curr Opin Microbiol, 12:252-260 (2009); Jones et al., Curr Opin Chem Biol, 13:216-223 (2009); Udwary et al., Proc Natl Acad Sci USA, 104:10376-10381 (2007)). This, combined with further genetic screening programs, suggests that only a fraction of the potential natural products produced in bacteria have been identified (Gust, Methods Enzymol, 458:159-180 (2009); Wilkinson et al., Nat Chem Biol, 3:379-386 (2007); Baltz, Antonie Van Leeuwenhoek, 79:251-259 (2001)). The cause for this lack in production is complex. First, media and environmental stimuli can contribute to bacterial secondary metabolism either up- or down-regulating the production of specific metabolites based on external cues or morphological responses (van Wezel et al., Appl Environ Microbiol, 72:5283-5288 (2006)). Second, evolutionary pressures are often key in regulating a microbe's ability to access secondary metabolism (te Poele et al., Antonie Van Leeuwenhoek, 94:127-143 (2008); Demain, Int Microbiol, 1:259-264 (1998); Hopwood, Philos Trans R Soc London, Ser B, 324: 549-562 (1989)). Mutagenesis offers a strong potential to circumvent the lack in production (Wang et al., J Nat Prod, 70:402-406 (2007); Malina et al., J Antibiot, 38:1204-1210 (1985); Lee et al., Lett Appl Microbiol, 34:370-375 (2002); Lyutskanova et al., Appl Biochem Microbiol, 41:165-168 (2005); Kieser et al., Practical *Streptomyces* Genetics (2000); Lalm et al., Crit Rev Microbiol, 22:201-255 (1996); Hopwood, Philos Trans R Soc London, Ser B, 290:313-328 (1980)), as mutant strains can be directed, through associated screening efforts, to enhance production. In this study, we demonstrate how applications of such strain improvement techniques can be used to access the production of new metabolites.

The present disclosure relates to new bioactive spirotetronates that arose from the application of mutagenesis (The following references provide examples of the application of mutagensis methods to *S. platensis* and related streptomycetes: Wang et al., J Nat Prod, 70:402-406 (2007); Malica et al., J Antibiot (Tokyo), 1204-1210 (1985); Lee et al., Lett Appl Microbiol, 34:370-375 (2002); Lyutskanova et al., Appl Biochem Microbiol, 41:165-168 (2005) and clonal selection techniques (Pang et al., Antimicrob Agents Chemother, 48:575-588 (2004); Kieser et al., Practical *Streptomyces* Genetics, 102-103 (2000); Baltz, Antonie van Leeuwenhoek, 79:251-259 (2001)) to strains of *S. platensis*.

Spirohexenolide A belongs to a large class of spirotetronate natural products that includes A88696F (Bonjouklian, Tetrahedron Lett, 34:7861-7864 (1993)), abyssomicins (Bister et al., Angew Chem, Int Ed, 43:2574-2576 (2004)), chlorothricin (Brufani et al., Helv Chim Acta, 55:2094-2102 (1972)), decatromicins (Momose et al., J Antibiot, 52:787-796 (1999)), pyrrolosporin A (Schroeder et al., J Antibiot, 49:865-872 (1996)), PA-46101-A (Matsumoto et al., J Antibiot, 43:739-747 (1990)), tetronomycin (Keller-Juslén et al., J Antibiot, 35:142-150 (1982)), and versipelostatin (Park et al., Org Lett, 9:1457-1460 (2007)). While structural similarities exist, spirohexenolide A contains a unique and functionally compact carbon framework and offers a new carbon skeleton. Its salient features include a unique pyran, a high degree of unsaturation, and a tetra-substituted olefin juncture between its tetronic acid and the adjacent pyran. This juncture can be the result of an intramolecular dehydration reaction of an appropriately spaced distal alcohol onto the 3-keto portion of the spirotetronate, such as in carolic acid (Clutterbuck et al., Biochem J, 29:300-321 (1935)).

The biosynthesis of spirohexenolide A can be derived through a late-stage intramolecular Diels-Alder (IMDA) cycloaddition. Application of IMDA reactions to the syntheses of spirotetronate natural products is well established, such as in the total synthesis of abyssomicin C by Sorensen (Zapf et al., Angew Chem, Int Ed, 44:6533-6537 (2005)) and an approach to chlorothricolide by Yoshii (Takeda et al., J Org Chem, 55:3431-3434 (1990)). To date, the biosynthetic gene clusters of four metabolites of this family (chlorothricin (Jia et al., Chem Biol, 13:575-585 (2006)), kijanimicin (Zhang et al., J Am Chem Soc, 129:14670-14683 (2007)), tetronomycin (Demydchuk et al., ChemBioChem, 9:1136-1145 (2008)), and tetrocarcin A (Fang et al., J Bacteriol, 190:6014-6025 (2008))) have been elucidated and several of these pathways include a putative IMDA biogenesis. The isolation of spirohexenolide B suggests that oxidation at C-8 arose at a late stage by oxidation via a cytochrome P450 or related enzyme (Related P450 oxidations: Machida et al., J Biosci Bioeng, 107:596-598 (2009); Lin et al., J Am Chem Soc, 131:6332-6333 (2009); Henry et al., J Am Chem Soc, 127:3724-3733 (2005)). The chemical properties of the biosynthetic product can be modified by adjusting the chemical structure of the starting materials and such methods are well known in the art.

The present disclosure relates to the identification and isolation of two new spirotetronate polyketides, spirohexenolide A and B, from *S. platensis*. Their structures have been elucidated through spectroscopic and X-ray crystallographic analyses. The present disclosure also relates to the determination that mutagenesis can be used in conjunction with culture optimization to provide viable quantities of these trace metabolites (Bode et al., ChemBioChem, 3:619-627 (2002)). Activity analyses indicated that spirohexenolide A displays significant activity against tumor cell growth with a unique specificity to select tumor cell lines (cf. NCI-60 cell line screening data in the Supporting Information). The fact that spirohexenolide B ($GI_{50}$ value of 61.2±7.8 µM in HCT116 cells) also displays comparable activity to spirohexenolide A ($GI_{50}$ value of 36.0±5.1 µM in HCT116 cells) when screened in house using the MTT assay indicates that the C-8 hydroxyl group can serve as a site for reporter attachment for identifying its cellular targets (Hughes et al., Angew Chem, Int Ed, 48:728-732 (2009); Leslie et al., Chem Soc Rev, 37:1347-1360 (2008); Alexander et al., ChemBioChem, 7:409-416 (2006)). The combination of the unique structure and activity of these spirohexenolides serve as the starting point for the development of both chemical synthesis and mechanism of action studies.

The present disclosure provides for the compound of formula (I) or a pharmaceutically acceptable salt, metabolite, prodrug or stereoisomer thereof:

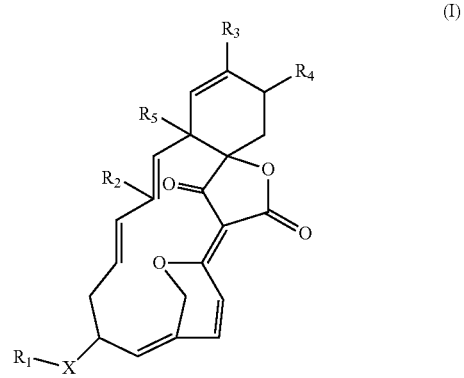

(I)

wherein X is a direct bond, —C—, —O—, —C(=O)—, —O—C(=O)—, —O—C(=O)—O—, —S—, or —C(=O)NH—;

$R_1$ is H, $C_1$-$C_6$ alkyl, $C_2$-$C_6$ alkenyl, $C_2$-$C_6$ alkynyl, $C_1$-$C_6$ alkoxy, —$CF_3$, aryl, heteroaryl, or a label;

$R_2$, $R_3$, $R_4$, and $R_5$ are independently H, $C_1$-$C_6$ alkyl, $C_2$-$C_6$ alkenyl, $C_2$-$C_6$ alkynyl, $C_1$-$C_6$ alkoxy, halo, —$CF_3$, —$OR_6$, —$C(O)R_6$, —$NHC(O)R_6$, —$C(O)OR_6$, —$OC(O)R_6$, —$NR_7R_8$, —$C(O)NR_7R_8$, —$NHR_6C(O)NR_7R_8$, or —$SO_2NR_7R_8$; and $R_6$, $R_7$, and $R_8$ are independently H, $C_1$-$C_6$ alkyl, $C_2$-$C_6$ alkenyl, $C_2$-$C_6$ alkynyl, $C_1$-$C_6$ alkoxy, halo, aryl, or heteroaryl, each being optionally substituted with one or more of the following substitutents: halo or $C_1$-$C_6$ alkyl.

In some aspects, the present disclosure provides for compound having the structure of formula (I), w wherein $R_1$ is H or —$C(O)CH_3$.

In certain aspects, the present disclosure provides for compounds having the structure of formula (IV):

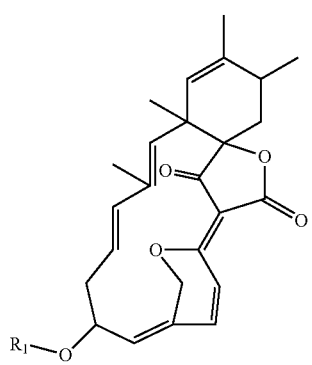

(IV)

In certain aspects, the present disclosure provides for compound having the structure of formula (V):

(V)

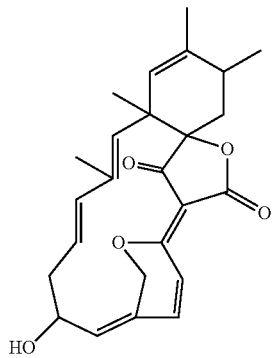

In further aspects, the present disclosure provides for compound having the structure of formula (VI):

(VI)

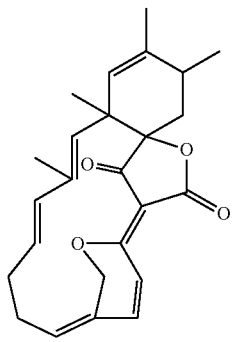

In one aspect, the present disclosure provides for a compound referred to as spirohexenolide A, which has the structure and stereochemical configuration of formula (VII):

(VII)

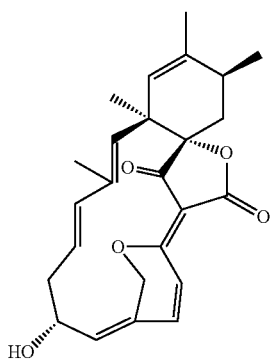

In one aspect, the present disclosure provides for a compound referred to as spirohexenolide B, which has the structure and stereochemical configuration of formula (VIII):

(VIII)

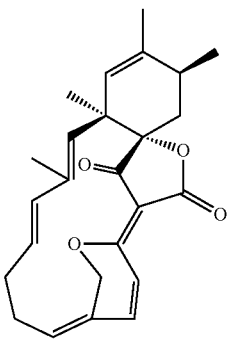

Chemical moieties referred to as univalent chemical moieties (e.g., alkyl, aryl, etc.) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —$CH_2CH_2$—, which is equivalent to an "alkylene" group). Similarly, under circumstances where a divalent moiety is required, those skilled in the art will understand that the term "aryl" refers to the corresponding divalent arylene group.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

"Acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Acyl" refers to branched or unbranched hydrocarbon fragments terminated by a carbonyl —(C=O)— group containing the specified number of carbon atoms. Examples include acetyl [$CH_3C$(=O)—, a $C_2$acyl] and propionyl [$CH_3CH_2C$(=O)—, a $C_3$acyl].

"Alkanoyloxy" refers to an ester substituent wherein the non-carbonyl oxygen is the point of attachment to the molecule. Examples include propanoyloxy [($CH_3CH_2C$(=O)—O—, a $C_3$alkanoyloxy] and ethanoyloxy [$CH_3C$(=O)—O—, a $C_2$alkanoyloxy].

"Alkoxy" refers to an O-atom substituted by an alkyl group, for example, methoxy [—$OCH_3$, a $C_1$alkoxy].

"Alkoxyalkyl" refers to an alkylene group substituted with an alkoxy group. For example, methoxyethyl [$CH_3OCH_2CH_2$—] and ethoxymethyl ($CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2OC$(=O)—, a $C_3$alkoxycarbonyl] and methoxycarbonyl [$CH_3C$(=O)—, a $C_2$alkoxycarbonyl].

"Alkyl," "alkenyl," and "alkynyl," refer to straight and branched chain aliphatic groups having from 1 to 30 carbon atoms, or preferably from 1 to 15 carbon atoms, or more preferably from 1 to 6 carbon atoms, each optionally substituted with one, two or three substituents depending on valency. Examples of such groups include, without limitation, methyl, ethyl, propyl, isopropyl, butyl, tert-butyl, isobutyl, pentyl, hexyl, vinyl, allyl, isobutenyl, ethynyl, and propynyl.

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, and biaryl groups, all of which can be optionally substituted. Phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which can be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which can be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which can be optionally substituted.

"Halogen" refers to a chloro, bromo, fluoro or iodo atom radical. The term "halogen" also contemplates terms "halo" or "halide".

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present invention.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing a hydroxy (—OH) group. Examples include hydroxymethyl (—$CH_2OH$, a $C_1$hydroxyalkyl) and 1-hydroxyethyl (—$CHOHCH_3$, a $C_2$hydroxyalkyl).

"Thioalkyl" refers to a sulfur atom substituted by an alkyl group, for example thiomethyl ($CH_3S$—, a $C_1$thioalkyl).

A "substituted" moiety is a moiety in which one or more hydrogen atoms have been independently replaced with another chemical substituent. As a non limiting example, substituted phenyl groups include 2-fluorophenyl, 3,4-dichlorophenyl, 3-chloro-4-fluorophenyl, and 2-fluoro-3-propylphenyl. In some instances, a methylene group (—$CH_2$—) is substituted with oxygen to form a carbonyl group (—CO).

An "optionally substituted" group can be substituted with from one to four, or preferably from one to three, or more preferably one or two non-hydrogen substituents. Examples of suitable substituents include, without limitation, alkyl, alkenyl, alkynyl, cycloalkyl, heterocycloalkyl, aryl, heteroaryl, aroyl, halo, hydroxy, oxo, nitro, alkoxy, amino, imino, azido, mercapto, acyl, carbamoyl, carboxy, carboxamido, amidino, guanidino, sulfonyl, sulfinyl, sulfonamido, formyl, cyano, and ureido groups.

Compounds of the present invention can exist as stereoisomers, wherein asymmetric or chiral centers are present.

Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present disclosure contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compositions described herein can comprise racemic mixtures of enantiomers as well as compositions comprising each enantiomer individually, substantially free of the other enantiomer(s). By "substantially free" it is meant that the composition comprises less than about 25%, 15%, 10%, 8%, 5%, 3%, or 1% of the minor enantiomer(s) or diastereomer(s). Methods for synthesizing and isolating stereoisomers are known in the art.

In some aspects, the present disclosure provides for a compound having the structure of formula (II):

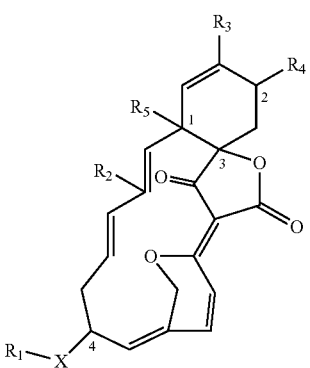

(II)

wherein carbon 1 is in the R configuration, S configuration, or a combination thereof.

In further aspects, carbon 2 as provided in formula (II) is in the R configuration, S configuration, or a combination thereof.

In further aspects, carbon 2 as provided in formula (II) is in the R configuration, S configuration, or a combination thereof.

In further aspects, carbon 2 as provided in formula (II) is in the R configuration, S configuration, or a combination thereof.

In certain aspects, the present disclosure provides for compounds having the structure and stereochemical configuration of formula (III):

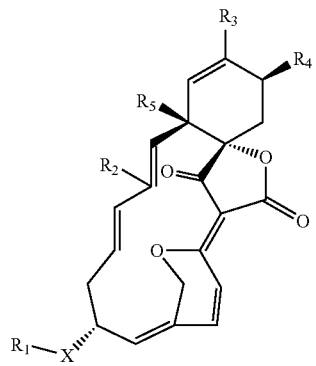

(III)

and pharmaceutically acceptable analogues, salts, prodrugs, metabolites.

Also, moieties disclosed herein which exist in multiple tautomeric forms include all such forms encompassed by a given tautomeric structure.

Particular geometric isomers (e.g., E or Z isomers) disclosed herein include the E or Z isomer substantially free from the other isomer as well as mixtures of E and Z isomers in varying ratios. For example, in some preferred aspects, compounds provided herein comprise the (Z)-isomer substantially free from the (E)-isomer.

Certain E and Z geometric isomers can be interconverted by photolysis, photo irradiation or exposure to free radicals or certain solvents (see e.g., Ishida et al., Tetrahedron Lett 30:959 (1989)). For example, exposure of some (E) compounds to DMSO facilitates their conversion to the Z form.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention can be used in either the free base or salt forms, with both forms being considered as being within the scope of the present invention. Representative salts include hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These can include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge et al., "Pharmaceutical Salts," J. Pharm. Sci. 66:1-19 (1977), which is incorporated herein by reference.)

Compounds provided herein can form useful salts with inorganic and organic acids, such as hydrochloric, sulfuric, acetic, lactic, or the like, and with inorganic or organic bases such as sodium or potassium hydroxide, piperidine, morpholine, ammonium hydroxide, or the like. Pharmaceutically acceptable salts of compounds provided herein can be prepared using procedures familiar to those skilled in the art.

In further aspects, spirohexenolide analogues of formula (I) are provided along with pharmaceutically acceptable analogues, salts, prodrugs, metabolites, and stereoisomers thereof. In general, $R_1$, $R_2$, $R_3$, $R_4$, and $R_5$ in formula (I) can independently comprise any functional moiety or substituent which allows for the formation of a stable compound having one or more beneficial properties or activities characteristic of spirohexenolide A. Examples of such substituents include, but are not limited to, optionally substituted aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; and —$CH_2SO_2CH_3$. In some aspects, the R group linkage is an ester, an ether, or a phenolic linkage.

A "prodrug" refers generally to a compound that is rapidly transformed in vivo to yield a parent compound, such as a novel polyketide compound provided herein, for example by enzymatic or non-enzymatic hydrolysis. A variety of methods and systems are known in the art for producing prodrugs having desired properties in vivo.

In another aspect, methods are provided herein for preparing spirohexenolide A, comprising culturing a microorganism having the identifying characteristics of *Streptomyces platensis* under suitable conditions, allowing spirohexenolide A to accumulate in the culture medium, and isolating spirohexenolide A from the culture medium.

Also provided herein are biologically pure cultures of a microorganism capable of producing spirohexenolides substantially free from biologically active contaminants. In some aspects, the microorganism is *Streptomyces platensis*. In further aspects, the microorganism is strain MJ1A1 or MJ1A2 of *Streptomyces platensis*.

In some aspects, the present disclosure provides a process for preparing the compounds of the present disclosure, the process comprising culturing a microorganism having the identifying characteristics of *Streptomyces platensis* under suitable conditions, allowing the compound to accumulate in the culture medium, and isolating the compound from the culture medium. In certain aspects, the process further comprises the steps of inducing mutations in *Streptomyces platensis* microorganisms by exposing the microorganisms to a mutagen, selecting the resulting microorganisms having a desired trait, and culturing the selected organisms. In further aspects, the mutagen is ultraviolet irradiation, ionizing radiation, or a chemical mutagen. In yet further aspects, the desired characteristic is decreased contact inhibition. In certain aspects, the microorganism is strain MJ1A1 or MJ1A2 of *Streptomyces platensis*. In some aspects, the present disclosure provides for compounds prepared by the processes of the present disclosure.

According to the present methods, any suitable mutagen can be used, i.e., environmental conditions that cause genetic mutations in the cells can be used. Methods for mutagenizing cells are well known in the art and include chemical treatment, exposure to ultraviolet light, exposure to x-rays, and retroviral insertional mutagenesis. Chemical mutagens include ethylmethane sulfonate (EMS), N-methyl-N'-nitro-N-nitrosoguanidine, 2-methoxy-6-chloro-9-[3-(ethyl-2-chloroethyl)aminopropylamino]acridine-2HCl, 5-bromouracil, acridine, and aflatoxin. See Lawrence, Methods Enzymol. 194:273-281, 1991.

In certain aspects, the present disclosure provides for compounds optionally having a label at $R_1$. The compounds of the present disclosure can be labeled using any suitable means. For instance, the compounds can be labeled with an immunological label, a fluorescent label, a chemiluminescent label, a radioisotope label, an enzyme label, a particulate label, a colorimetric label, or an energy transfer agent.

In some aspects, the present disclosure provides for methods of screening for proteins that bind to the compounds of the present disclosure comprising exposing a cancerous tissue to a compound comprising a label and detecting the presence of the labeled compound.

In another aspect, therapeutic methods are provided herein comprising administering to a patient in need of treatment a therapeutically effective amount of a spirohexenolide. Methods provided herein can be used to treat any disease or condition amenable to treatment with a spirohexenolide.

In some aspects, the present disclosure provides for methods of treating cancer, comprising administering a therapeutically effective amount of a compound of the present disclosure, or a pharmaceutically acceptable salt, metabolite, prodrug or stereoisomer thereof, to a subject in need of treatment.

In one aspect, the present disclosure provides for methods of treating cancer comprising administering the compound having the structure and stereochemical configuration of formula (X) or a pharmaceutically acceptable salt, metabolite, prodrug or stereoisomer thereof, to a subject in need of treatment:

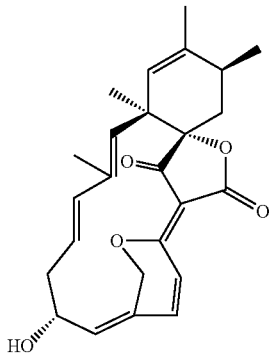

(X)

In further aspects, methods are provided herein for treating a tumor and/or inhibiting growth and/or metastasis of tumor cells. In further aspects, methods are provided herein for inhibiting the proliferation, growth, and/or migration of cancer cells and/or cancer-related angiogenesis.

The term "treating" as used herein can comprise prevention, amelioration, alleviation, and/or elimination of a condition being treated and/or one or more symptoms thereof, as well as improvement in the overall well being of a subject, as measured by objective and/or subjective criteria.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In another aspect, pharmaceutical compositions are provided comprising a therapeutically effective amount of a spirohexenolide, optionally in combination with a second active agent, and one or more pharmaceutically acceptable excipients. Preferably, the pharmaceutical compositions are suitable for administration to human subjects.

In some aspects, the present disclosure provides for pharmaceutical compositions comprising a therapeutically effective amount of a compound of the present disclosure or a pharmaceutically acceptable salt, metabolite, prodrug or stereoisomer thereof, and a pharmaceutically acceptable excipient.

In one aspect, the present disclosure provides for pharmaceutical compositions comprising a therapeutically effective amount of a compound having the structure and stereochemical configuration of formula (IX):

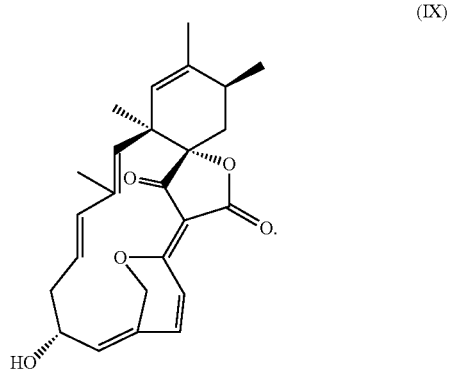 [SMILES: CC1=C[C@]2(C)/C=C(C)/C=C/C[C@@H](O)/C=C3C=C/C(=C4\C(=O)O[C@]2(C[C@@H]1C)C4=O)OC/3]

(IX)

As used herein, the term "pharmaceutically acceptable excipient" includes any excipient known as being suitable for pharmaceutical application. Suitable pharmaceutical excipients and formulations are well known in the art and are described, for example, in Remington's Pharmaceutical Sciences (19th ed.) (Genarro, ed. (1995) Mack Publishing Co., Easton, Pa.). The pharmaceutically acceptable carrier can include, for example, any and all solvents, disintegrants, binders, lubricants, glidants, emollients, humectants, thickeners, silicones, flavoring agents, water, and the like.

The compounds of the present invention have utility in pharmacological compositions for the treatment and prevention of many diseases and disorders characterized by an MIF response, whereby MIF is released from cellular sources and MIF production is enhanced. A compound of the invention can be administered to a human patient by itself or in pharmaceutical compositions where it is mixed with suitable carriers or excipients at doses to treat or ameliorate various conditions characterized by MIF release. A therapeutically effective dose further refers to that amount of the compound sufficient to inhibit MIF tautomerase activity and MIF bioactivity, it being understood that such inhibition can occur at different concentrations such that a person skilled in the art could determine the required dosage of compound to inhibit the target MIF activity. Therapeutically effective doses can be administered alone or as adjunctive therapy in combination with other treatments for tumor growth or associated diseases. Techniques for the formulation and administration of the compounds of the instant application can be found in "Remington's Pharmaceutical Sciences" Mack Publishing Co., Easton, Pa., latest addition.

Suitable routes of administration can, for example, include topical, cutaneous, oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. In an embodiment, topical administration utilizes excipients such as creams, emulsifiers, and oils. Further embodiments, topical administration utilizes dermal absorption enhancers selected from the group consisting of dimethyl sulfoxide, menthol, lauryl alcohol, lauric acid, arachidonic acid and $C_1O-C_2O$ polyhydroxy acids and thymol.

Furthermore, one can administer a compound of the present invention in a targeted drug delivery system, for example in a liposome.

The pharmaceutical compositions and compounds of the present invention can be manufactured in a manner that is itself known, e.g., by means of conventional mixing, dissolving, dragee-making, levitating, emulsifying, encapsulating, entrapping, or lyophilizing processes. Pharmaceutical compositions for use in accordance with the present invention thus can be formulated in conventional manner using one or more physiologically acceptable carriers comprising excipients and auxiliaries that facilitate processing of the active compounds into preparations, which can be used pharmaceutically. Proper formulation is dependent upon the route of administration chosen.

For injection, the compounds of the invention can be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are known in the art.

For oral administration, the compounds can be formulated readily by combining the active compounds with pharmaceutically acceptable carriers well known to those in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the compound with a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Liposomes and emulsions are well known examples of delivery vehicles or carriers for hydrophobic drugs. Certain organic solvents such as dimethylsulfoxide also can be employed, although usually at the cost of greater toxicity. Additionally, the compounds can be delivered using a sustained-release system, such as semipermeable matrices of solid hydrophobic polymers containing the therapeutic agent. Various forms of sustained-release materials have been established and are well known by those skilled in the art. Sustained-release capsules can, depending on their chemical nature, release the compounds for a few weeks up to over 100 days. Depending on the chemical nature and the biological stability of the therapeutic reagent, additional strategies for protein stabilization can be employed.

The pharmaceutical compositions also can comprise suitable solid- or gel-phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as neutralizers of MIF activity can be provided as salts with pharmaceutically compatible counterions. Pharmaceutically compatible salts can be formed with many acids, including but not limited to hydrochloric, sulfuric, acetic, lactic, tartaric, malic, succinic, etc.; or bases. Salts tend to be more soluble in aqueous or other protonic solvents than are the corresponding free base forms. Examples of pharmaceutically acceptable salts, carriers or excipients are well known to those skilled in the art and can be found, for example, in Remington's Pharmaceutical Sciences, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate and malate salts, and the like.

In some aspects, a therapeutically effective amount of a spirohexenolide can be estimated based on results from experiments conducted in cell culture, in an animal model, or in another model system. Various conversion factors, formulas, and methods for determining human dose equivalents are known in the art and examples can be found, e.g., in Freireich et al., Cancer Chemother Repts 50(4): 219 (1966), Monro et al., Toxicology Pathology, 23: 187-98 (1995), Boxenbaum and Dilea, J. Clin. Pharmacol. 35: 957-966 (1995), and Voisin et al., Reg. Toxicol. Pharmacol., 12(2): 107-116 (1990), which are herein incorporated by reference. In some aspects, a therapeutically effective amount is estimated as an amount that achieves a peak concentration within a target tissue, using a particular mode of administration, at or above the $IC_{50}$ or $EC_{50}$ concentration for a desired effect using the spirohexenolide being administered.

Having now generally described various aspects and embodiments of the invention, the same will be more readily understood through reference to the following examples which are provided by way of illustration, and are not intended to be limiting, unless specified.

EXEMPLARY ASPECTS

Example 1

Isolation, Structure Elucidation, and Antitumor Activity of Spirohexenolides A and B Mutagenesis of *S. platensis*.

Spore suspensions were prepared from glycerol stocks of *S. platensis* MJ. While a series of strains were examined, compounds 1 and 2 were obtained from this parent strain and its mutants.

A 1 µL aliquot of these suspensions was added to 1 mL of sterilized water and further diluted by addition of 10 µL of this solution into 10 mL of water to yield a solution containing approximately $6 \times 10^5$ spores/mL. This solution was then poured onto a sterile 9 cm glass Petri dish and UV irradiated (Stratalinker 1800) at 8000 µJ at a distance of 12 cm while being stirred. Samples were taken every 6 s over a 3 min period. After serial dilution of UV-irradiated spore suspension in deionized $H_2O$, the sample was spread onto Bennett's agar (1.0% w/v glucose, 0.2% w/v pancreatic digest of casein, 0.1 w/v of yeast extract, 0.1% w/v beef extract, 1.5% w/v of agar in deionized $H_2O$ at pH 7.0), YEMED agar (0.4% w/v yeast extract, 1.0% w/v malt extract, 0.4% w/v glucose, 1.5% w/v agar in deionized $H_2O$ at pH 7.2), and ISP4 agar (1.0% w/v soluble starch, 0.2% w/v $CaCO_3$, 0.1% w/v $K_2HPO_4$, 0.1% w/v $MgSO_4 \cdot 7H_2O$, 0.1% w/v NaCl, 0.2% w/v $(NH_4)_2SO_4$, 0.001% w/v $FeSO_4 \cdot 7H_2O$, 0.001% w/v $MnCl_2 \cdot 4H_2O$ and 0.001% w/v of $ZnSO_4 \cdot 7H_2O$ in deionized $H_2O$ at pH 7.2) for examining the morphologically differentiating colonies. To prevent photoreactivation, the plates were wrapped with foil for 24 h and then incubated at 30° C. for 15 days.

Mutant Screening Identifies Producer Strains *S. platensis* MJ1A1 and MJ1A2.

After 15 days of incubation, survival colonies were transferred onto R2YE media (10.3% w/v sucrose, 0.5% w/v yeast extract (Difco), 0.01% w/v casaminoacids (Difco), 0.025% w/v $K_2SO_4$, 1.01% w/v $MgCl_2.6H_2O$, 1% w/v glucose, 0.025% w/v $KH_2PO_4$, 0.29% w/v $CaCl_2.2H_2O$, 0.0008% w/v $ZnCl_2$, 0.004% w/v $FeCl_3.6H_2O$, 0.0004% w/v $CuCl_2.2H_2O$, 0.0004% w/v $MnCl_2.4H_2O$, 0.0004% w/v $Na_2B_4O.10H_2O$, 0.0004% w/v $(NH_4)_5Mo_7O_{24}.4H_2O$ 0.3% w/v L-proline, 0.573% w/v N-tris(hydroxymethyl)methyl-2-aminoethanesulfonic acid (TES), 0.005% v/v 1 N NaOH to provide a pH 7.2). Once the mutants had sporulated, agar cones (3 mm OD×5 mm height) were excised containing a single colony and stamped on top of a glucose basal salt (1% g of glucose, 0.01% yeast extract, 1.5% agar, 0.02% $MgSO_4.7H_2O$, 0.001% NaCl, 0.001% $FeSO_4.7H_2O$, 0.001% $MnSO.4H_2O$ 0.2% $NH_4Cl$, 0.465% $K_2HPO_4$, 0.09% of $KH_2PO_4$ at pH 7.0) agar seeded with ~8×10$^7$ of *Bacillus subtilis* 6633 per cm$^2$. After incubation at 37° C. for 24 h, colonies showing a zone of inhibition were compared against their parent strain. Strains MJ1A, MJ2B and MJ6 (FIG. 1a) were obtained with this method.

Minimum Inhibitory Concentration (MIC) Assay of Spirohexenolide A (1), using *Bacillus subtilis* 6633.

Spirohexenolide A (1) in dimethyl sulfoxide (DMSO) was diluted to 10, 15, 30, 60, 120, 250, 500, and 1000 μg/mL stocks in tryptic soy broth with a final concentration of 1% DMSO. *B. subtilis*, cultured for 18 h at 37° C. in tryptic soy broth, was inoculated at 1/10000 to a final volume of 200 μL per well on a 96 well plate and then treated with 2 μL of a stock solution of 1 (10, 15, 30, 60, 120, 250, 500, and 1000 μg/mL in tryptic soy broth containing 1% DMSO). The plate was incubated in 37° C. for 18 h, indicating that pure 1 had an MIC value of 12.25 μM (no visible bacterial growth). The compound was tested in duplicates. Negative control comprised of DMSO solvent did not show any effect on the bacterial growth.

Culturing of Spirohexenolide A (1) from *S. platensis* Strain MJ1A1.

A single colony of *S. platensis* MJ1A1 grown on yeast extract-malt extract-dextrose (YEMED) agar was resuspended in 50 μL of sterilized water, using a sterilized pellet pestle, and inoculated into 3 mL of tryptic soy broth (BD Biosciences) and shaken at 220 rpm at 28° C. for 40 h. An aliquot (2 mL) of this starter culture was transferred into a 250 mL baffled Erlenmeyer flask containing 100 mL of seed medium containing 1% w/v glucose, 2.4% w/v soluble starch, 0.3% w/v beef extract, 0.5% w/v tryptone, 0.5% w/v yeast extract, and 2.0% w/v $CaCO_3$ adjusted to pH 7.2. After shaking the seed medium for 48 h at 220 rpm and 28° C., a 50 mL aliquot was transferred to a 2.8 L baffled Erlenmeyer flask containing 500 mL of fermentation media (6% w/v soluble starch, 1% w/v dry yeast, 1% w/v β-cyclodextrin, 0.2% w/v $CaCO_3$ adjusted to pH 6.8 prior to sterilization) and 2% w/v of Amberlite XAD-16 resin (Alfa Aesar) that was washed repetitively with deionized water prior to sterilization. The fermentation media was shaken for 72 h at 220 rpm at 28° C. The cultures were filtered through cheesecloth to collect the resin. The resin was then returned to the baffled flask and acetone (250 mL) and EtOAc (250 mL) were added. The flask was shaken for 2 h at 220 rpm. The resin was filtered again through cheesecloth, and the filtrate was concentrated on a rotary evaporator until only insoluble solids and water remained. EtOAc was added until most of the solids were dissolved, and the mixture was poured into a reparatory funnel. The aqueous layer was extracted with additional EtOAc (2×100 mL), and the combined organic layers were concentrated to provide a crude extract. Crude extract was dissolved in a minimum amount of 1:1 hexanes:EtOAc (sonication was used to facilitate dissolution). A 2 in. ID column containing silica gel (EM Sciences) was packed with 1:1 hexanes:EtOAc, and the solution of the crude extract was loaded. The column was run with 1:1 hexanes:EtOAc for at least two column volumes before EtOAc was used to elute 1 with $R_f$ 0.29 (EtOAc). Compounds 1 and 2 could be visualized by ceric ammonium molybdate, 2,4-dinitrophenylhydrazine, iodine, and potassium permanganate stains, and short-wave UV (excitation at 254 nm). Pure spirohexenolide A (1) was obtained after a second flash column, using a gradient from hexanes to EtOAc or trituration with small amounts of absolute ethanol.

Isolation of Spirohexenolide B (2) from Cultures of *S. platensis* Strain MJ1A1.

*S. platensis* strain MJ1A1 was cultured in the same manner on the same scale used to produce spirohexenolide A (1), (above), but the fermentation media was supplemented with 10% w/v of Amberlite XAD-16 resin (Alfa Aesar®) that was washed repetitively with deionized water prior to sterilization. The fermentation media was shaken for 72 h at 220 rpm at 28° C. The crude extract of the resin was processed in the same manner as used for the isolation of spirohexenolide A (1), as described in the preceding paragraph. A 2 in. i.d. column containing silica gel (EM Sciences) was packed with 1:1 hexanes:EtOAc, and the solution of the crude extract was loaded. The column was run with 1:1 hexanes:EtOAc for two column volumes, and spirohexenolide B (2) was obtained from the eluted and concentrated material by subjecting it to a second Flash purification on a 2 in. i.d. column with a gradient from hexanes to 1:1 hexanes:EtOAc with elution of 2 in 1:1 hexanes:EtOAc with $R_f$ 0.68 (EtOAc), followed by crystallization from either EtOH or a mixture of $CH_2Cl_2$ and hexanes to obtain yellow crystals.

Synthesis of Mosher Esters 3a and 3b.

The (S)- and (R)-MTPA derivatives 3a and 3b were prepared with use of a slight modification of the standard procedure (Dale et al., J Am Chem Soc, 95:512-519 (1973); Ohtani et al., J Am Chem Soc, 113:4092-4096 (1991)). (S)-MTPA ester 3a: To a sample of compound 1 (30.3 mg, 0.0743 mmol) in a dry 25 mL round-bottomed flask with a Teflon®-coated magnetic stirbar were added a few crystals of 4-dimethylaminopyridine and the flask was sealed with a rubber septum and flushed with argon. $CH_2Cl_2$ (3 mL) and pyridine (0.120 mL, 1.5 mmol) were added at room temperature, and the mixture was stirred until a yellow solution was achieved. Stirring was then continued as 70 μL of (R)-MTPA-Cl (0.374 mmol) was added via syringe at room temperature. After 30 min the solution turned dark green. After 50 min, TLC indicated a new compound had formed with $R_f$ 0.76 (EtOAc), and that compound 1 had been consumed. The reaction mixture was then poured into a reparatory funnel containing half-saturated $NaHCO_3$ (30 mL) and $CH_2Cl_2$ (20 mL), and the organic layer became yellow again upon shaking. The aqueous layer was extracted with another 20 mL of $CH_2Cl_2$ and the combined organic layers were dried over $Na_2SO_4$ and concentrated under reduced pressure. The residue was dissolved in 3:1 hexanes:EtOAc (5 mL), and standard flash chromatography with 3:1 hexanes:EtOAc provided pure 3a (16.3 mg, 35%). The same procedure was used on 1 and (S)-MTPA-Cl to make the (R)-MTPA ester 3b (13.5 mg, 40%).

Spirohexenolide A (1):

yellow needles, mp 280-285° C. dec; $[\alpha]^{25}_D$+551.3 (c 0.4, $CHCl_3$); UV $\lambda_{max}$ (MeOH) 339 (ϵ 8650), 236 (ϵ 25583) nm; IR (film) $v_{max}$ 3469, 1754, 1702, 1582, 1550, 1059, 1043, 988, and 968 cm$^{-1}$; ESIMS m/z 409.03 [M+H]$^+$, 431.03, [M+Na]$^+$; HR-EI-MS m/z 408.1947, [M]$^+$ (calcd for $C_{25}H_{28}O_5$ [M]$^+$, 408.1931); $^1$H and $^{13}$C NMR (Table 1).

TABLE 1

$^1$H, $^{13}$C, gCOSY, NOESY, and HMBC NMR Data[g] for Spirohexenolide A (1) in CDCl$_3$

| C/H no. | $\delta_H$ mult (J Hz)[a] | $\delta_C$ (mult)[b] | COSY[c] | NOESY[c] | HMBC[c,f] |
|---|---|---|---|---|---|
| 1 | | 169.3 (C) | | | |
| 2 | | 100.8 (C) | | | |
| 3 | | 165.7 (C) | | | |
| 4 | 7.44 d (10.0) | 120.3 (CH) | 5 | 5 | 3, 6 |
| 5 | 7.02 d (10.0, <1) | 142.1 (CH) | 4, 21a | 4, 7 | 3, 6, 7, 21 |
| 6 | | 126.7 (C) | | | |
| 7 | 5.72 d (8.4) | 139.3 (CH) | 8 | 5, 21b | 5, 21 |
| 8 | 4.60 m | 69.3 (CH) | 7, 9a, 9b | 9a, 9b, 10 | 9 |
| 9a | 2.60 m | | 8, 9b, 10 | 8, 9b, 10, 11[e] | 8, 10, 11 |
| 9b | 2.17 dt (10.6, 12.3) | 42.6 (CH$_2$) | 8, 9a, 10 | 8, 9a, 10, 11 | 8, 10, 11 |
| 10 | 5.55 ddd (5.4, 10.6, 15.5) | 120.8 (CH) | 9a, 9b, 11 | 8[d], 9a, 9b, 13[e], 21a, 21b[d], 22[d] | 9, 11, 12 |
| 11 | 5.69 d (15.5) | 140.9 (CH) | 9a, 10 | 9b, 13 | 9, 10, 13, 22 |
| 12 | | 136.2 (C) | | | |
| 13 | 5.07 s | 134.8 (CH) | 22 | 10, 11, 15[e], 23[e] | 11, 14, 15, 22, 23 |
| 14 | | 44.3 (C) | | | |
| 15 | 5.29 s | 128.0 (CH) | 17, 24 | 13, 23, 24 | 13, 14, 17, 19, 24 |
| 16 | | 133.4 (C) | | | |
| 17 | 2.39 m | 33.5 (CH) | 15, 18a, 18b, 25 | 18a, 25 | 15, 16, 18, 19, 25 |
| 18a | 2.35 m | 33.3 (CH$_2$) | 17, 18b | 17, 18b, 23 | 14, 17, 19, 20, 25 |
| 18b | 1.71 d (13.6) | | 17, 18a | 18a, 25 | 14, 16, 17, 19, 20, 25 |
| 19 | | 89.2 (C) | | | |
| 20 | | 196.0 (C) | | | |
| 21a | 4.73 d (12.5) | 64.8 (CH$_2$) | 5, 21b | 10, 21b[d] | 3, 5, 6, 7 |
| 21b | 4.57 d (12.5) | | 21a | 7, 10, 21a | 5, 6, 7 |
| 22 | 1.76 s | 14.1 (CH$_3$) | 13 | 10 | 11, 12 |
| 23 | 1.19 s | 27.2 (CH$_3$) | | 13, 15, 18a | 13, 14, 15, 19 |
| 24 | 1.76 s | 22.0 (CH$_3$) | 15 | 15, 25 | 15, 16, 17, 18 |
| 25 | 1.34 d (7.2) | 19.6 (CH$_3$) | 17 | 17, 18b, 24[d] | 16, 17, 18 |

[a] $^1$H NMR data were collected at 500 MHz.
[b] $^{13}$C NMR data were collected at 100 MHz.
[c] $^{13}$C NMR multiplicities were determined by the DEPT spectrum.
[c] gCOSY, HMBC, and NOESY spectra were collected at 800 MHz.
[d] Overlapping signals detected
[e] A weak crosspeak was detected.
[f] HMBC data were collected with an evolution delay optimized for $^{2,3}J_{CH}$ = 8 Hz.
[g] Spectra were collected at 296 K in CDCl$_3$.

Spirohexenolide B (2):

yellow rhomboid crystals recrystallized from CH$_2$Cl$_2$ and hexanes, mp 219-221° C. dec; IR (film) $\nu_{max}$ 2922, 2852, 1735, 1707, 1587, 1551, 1466, 1410 cm$^{-1}$; ESIMS m/z 392.91 [M+H]$^+$; HR-ESI-MS m/z 415.1888, [M+Na]$^+$ (calcd for C$_{25}$H$_{28}$O$_4$Na [M+Na]$^+$ 415.1885); $^1$H and $^{13}$C NMR (Table 2).

TABLE 2

$^1$H, $^{13}$C, gCOSY, and HMBC Data[e] for Spirohexenolide B (2) in C$_6$D$_6$

| C/H no. | $\delta_H$ mult (J, Hz)[a] | $\delta_C$ (mult)[b] | COSY[c] | HMBC[c,d] |
|---|---|---|---|---|
| 1 | | 168.9 (C) | | |
| 2 | | 101.1 (C) | | |
| 3 | | 165.5 (C) | | |
| 4 | 7.59 d (10.0) | 119.3 (CH) | 5 | 3, 6 |
| 5 | 6.20 d (10.0) | 142.2 (CH) | 4, 21b | 3, 6, 7, 21 |
| 6 | | 128.8 (C) | | |
| 7 | 4.97 t (8.5) | 135.4 (CH) | 8, 21a | |
| 8 | 1.53 m | 27.8 (CH$_2$) | 7, 9a, 9b | |
| 9a | 1.92 m | 32.3 (CH$_2$) | 8, 9b, 10 | |
| 9b | 1.40 m | | 8, 9a, 10 | |
| 10 | 5.16 ddd (4.9, 10.9, 15.4) | 125.3 (CH) | 9a, 9b, 11 | 12 |
| 11 | 5.46 d (15.4) | 139.7 (CH) | 10 | 13, 22 |
| 12 | | 135.5 (C) | | |
| 13 | 5.13 s | 134.8 (CH) | 22 | 11, 14, 15, 22, 23 |
| 14 | | 44.5 (C) | | |
| 15 | 5.33 s | 129.0 (CH) | 17, 24 | 17, 19, 24 |
| 16 | | 133.3 (C) | | |
| 17 | 2.10 m | 33.9 (CH) | 15, 18a, 18b, 25 | 16, 25 |
| 18a | 2.30 dd (8.6, 14.6) | 33.7 (CH$_2$) | 17, 18b | 14, 17, 19, 20, 25 |
| 18b | 1.62 d (14.6) | | 18a | 14, 16, 17, 19, 20, 25 |
| 19 | | 88.4 (C) | | |
| 20 | | 195.3 (C) | | |
| 21a | 4.13 d (12.6) | 63.4 (CH$_2$) | 5, 21b | 3, 5, 6, 7 |
| 21b | 3.72 d (12.6) | | 7, 21a | 6, 7 |

TABLE 2-continued $^1$H, $^{13}$C, gCOSY, and HMBC Data$^e$ for Spirohexenolide B (2) in C$_6$D$_6$

| C/H no. | $\delta_H$ mult (J, Hz)$^a$ | $\delta_C$ (mult)$^b$ | COSY$^c$ | HMBC$^{c,d}$ |
|---|---|---|---|---|
| 22 | 1.96 s | 14.6 (CH$_3$) | 13 | 11, 12 |
| 23 | 1.30 s | 27.4 (CH$_3$) |  | 13, 14, 15, 19 |
| 24 | 1.65 s | 22.0 (CH$_3$) | 15 | 15, 16, 17 |
| 25 | 1.43 d (6.9) | 19.9 (CH$_3$) | 17 | 16, 17 |

$^a$$^1$H NMR data were collected at 500 MHz.
$^b$$^{13}$C NMR data were collected at 125 MHz.
$^c$gCOSY and HMBC spectra were collected at 800 MHz.
$^d$The HMBC spectrum was collected with an evolution delay of $^{2,3}J_{CH}$ = 6 Hz.
$^e$Spectra were collected at 296 K in C$_6$D$_6$. Due to a slow decomposition of 2 in CDCl$_3$, C$_6$D$_6$ was required for extended times required to collect $^{13}$C NMR, HMBC, and HSQC data.

Spirohexenolide A (S)-MTPA derivative (3a):

yellow solid, mp 208-211° C. dec; $[\alpha]^{23}_D$+159.3 (c 1, CH$_2$Cl$_2$); IR (film) $\nu_{max}$ 2936, 1750, 1709, 1594, 1554, 1252, 1168, 1056, 1014, and 722 cm$^{-1}$; ESI-MS m/z: 624.92 [M+H]$^+$, 647.04 [M+Na]$^+$; HR-ESI-FT-MS (Orbit-trap-MS) m/z calcd for C$_{35}$H$_{35}$F$_3$O$_7$Na [M+Na]$^+$ 647.2227. found 647.2218; see the Supporting Information for $^1$H and $^{13}$C NMR spectroscopic data.

Spirohexenolide A (R)-MTPA derivative (3b):

yellow solid, mp 246-250° C. dec; $[\alpha]^{23}_D$+223.5 (c 1, CH$_2$Cl$_2$); IR (film) $\nu_{max}$ 2936, 1750, 1709, 1594, 1554, 1252, 1169, 1056, and 1014 cm$^{-1}$; ESI-MS m/z: 625.18 [M+H]$^+$, 647.21 [M+Na]$^+$; HR-ESI-FT-MS (Orbit-trap-MS) m/z calcd for C$_{35}$H$_{36}$F$_3$O$_7$ [M+H]$^+$ 625.2408 found 625.2419; see the Supporting Information for $^1$H and $^{13}$C NMR spectroscopic data.

Uptake and Localization in HeLa Cells.

HCT-116 cells (ATCC CCL-247) were cultured in Dulbecco's modification of Eagle's medium (DMEM) with 4.5 g L$^{-1}$ glucose, 4.5 g L$^{-1}$ L-glutamine, and 5% heat inactivated fetal calf serum (FCS) in glass-bottom dishes. Fluorescent images were collected on a Leica (Wetzlar, Germany) DMI6000 inverted confocal microscope with a Yokogawa (Tokyo, Japan) spinning disk confocal head, Orca ER High Resolution B&W Cooled CCD camera (6.45 μm/pixel at 1×) (Hamamatsu, Sewickley, Pa.), Plan Apochromat 40×/1.25 na and 63×/1.4 na objective, and a Melles Griot (Carlsbad, Calif.) Argon/Krypton 100 mW air-cooled laser for 488, 568, and 647 nm excitations. Confocal z-stacks were acquired in all experiments. Co-staining was conducted by treating cells exposed to 1 to either Syto 60 (nucleus), LysoTracker Red DND-99 (lysosomes), BODIPY TR glibenclamide (endoplasmic reticulum), or MitoTracker Red 580 (mitochondria) for 20 min and washing the cells three times with media and collecting images in two colors.

X-Ray Crystallography.

A yellow needle of compound 10.25×0.10×0.10 mm$^3$ in size was mounted on a Cryoloop™ with Paratone oil. Data were collected in a nitrogen gas stream at 100(2) K using φ and ω scans. Crystal-to-detector distance was 50 mm and exposure time was 10 s per frame with a scan width of 0.5°. Data collection was 99.3% complete to 67.00° in θ. A total of 7195 reflections were collected covering the indices, −8≤h≤8, −15≤k≤14, −13≤l≤13. A total of 3065 reflections were found to be symmetry independent, with an R$_{int}$ of 0.0366. Indexing and unit cell refinement indicated a primitive, monoclinic lattice. The space group was found to be P2(1) (No. 4). The data were integrated with the Bruker SAINT software program and scaled with the SADABS software program. Solution by direct methods (SIR-2004) produced a complete heavy-atom phasing model consistent with the proposed structure. All non-hydrogen atoms were refined anisotropically by full-matrix least-squares (SHELXL-97). All hydrogen atoms were placed with use of a riding model. Their positions were constrained relative to their parent atom by using the appropriate HFIX command in SHELXL-97.

A colorless plate of compound 20.33×0.28×0.08 mm$^3$ in size was mounted on a Cryoloop with Paratone oil. Data were collected in a nitrogen gas stream at 100(2) K, using φ and ω scans. Crystal-to-detector distance was 50 mm and exposure time was 10 s per frame with a scan width of 0.5°. Data collection was 99.9% complete to 25.00° in θ. A total of 24117 reflections were collected covering the indices, −8≤h≤8, −15≤k≤15, −27≤l≤27. A total of 7549 reflections were found to be symmetry independent, with an R$_{int}$ of 0.0363. Indexing and unit cell refinement indicated a primitive, monoclinic lattice. The space group was found to be P2(1). The data were integrated with the Bruker SAINT software program and scaled with the SADABS software program. Solution by direct methods (SIR-2004) produced a complete heavy-atom phasing model consistent with the proposed structure. All non-hydrogen atoms were refined anisotropically by full-matrix least-squares (SHELXL-97). All hydrogen atoms were placed with use of a riding model. Their positions were constrained relative to their parent atom by using the appropriate HFIX command in SHELXL-97.

Results

A panel of S. platensis strains from available culture collections were first evaluated. An antibiotic assay using the inhibition of Bacillus subtilis growth was eventually chosen (comparable methods have been used in the discovery of spirotetronate natural products (Schindler et al., Eur J Biochem, 39:591-600 (1973); Gary et al., J Bacteriol, 64:501-512 (1952); Sundaram et al., Biochim Biophys Acta, 192: 355-357 (1969))). Due to the presence of only traces of compound 1 from the parent strain (often less than 1 mg/L), we applied both UV irradiation and NTG (N-methyl-N'-nitrosoguanidine) chemical mutagenesis for strain improvement. From UV irradiation analysis, we identified three mutant strains, MJ1A (1A, FIG. 1a), MJ2B (2B, FIG. 1a), and MJ6 (6, FIG. 1a), that displayed an increased zone of inhibition over their parent S. platensis strain MJ (wt, FIG. 1a). Subsequent efforts led to the production of two stable morphologies of MJ1A noted as strains MJ1A1 and MJ1A2 (Pang et al., Antimicrob Agents Chemother, 48:575-588 (2004)). 16S rRNA gene sequence data indicated that MJ1A strain showed high sequence identity to S. platensis NBRC12901 (99%) (Shirling et al., Int J Syst Bacteriol, 18:279-392 (1968)), S. hygroscopicus subsp. glebosus LMG 19950 (99%) (Kumar et al., Int J Syst Evol Microbiol, 58:1369-1378 (2008)), S. libani subsp. rufus NBRC 15424 (99%) (Skerman et al., Int J Syst Bacteriol, 30:225-420 (1980)), and S. caniferus NBRC 15389 (99%) (Preobrazhenskaya, Int J Syst Bacteriol, 36:573-576 (1986)).

¹H NMR-guided fractionation was applied to extracts from cultures of the *S. platensis* MJ1A1 and *S. platensis* MJ1A2. Metabolite 1, with a unique signature of olefinic protons in the NMR spectrum, was identified in the ethyl acetate (EtOAc) extract from both cultures. TLC analysis indicated that metabolite 1 (lane 1, FIG. 1b) was more abundant in extracts from strains MJ1A1 (lane 2, FIG. 1b) and MJ1A2 (lane 3, FIG. 1b) than their parent strain *S. platensis* MJ (lane 4, FIG. 1b). Control experimentation indicated that 1 also did not appear in related strains such as FERM BP-8442 (lanes 5 and 6, FIG. 1b), indicating that the production of 1 was restricted to strains MJ1A1 and MJ1A2. Similarly, HPLC analyses using UV detection at 254 nm confirmed the presence of 1 in both parent (*S. platensis* strain MJ) and mutant strains but not in other strains of *S. platensis* (FIG. 1c). While 1 was observed in parent (traces) and mutant extracts, TLC evidence (FIG. 1b) indicates that the mutants offered a significant increase in production of 1 relative to their lipid content (lipids could not be detected under our HPLC methods).

Figure 2:
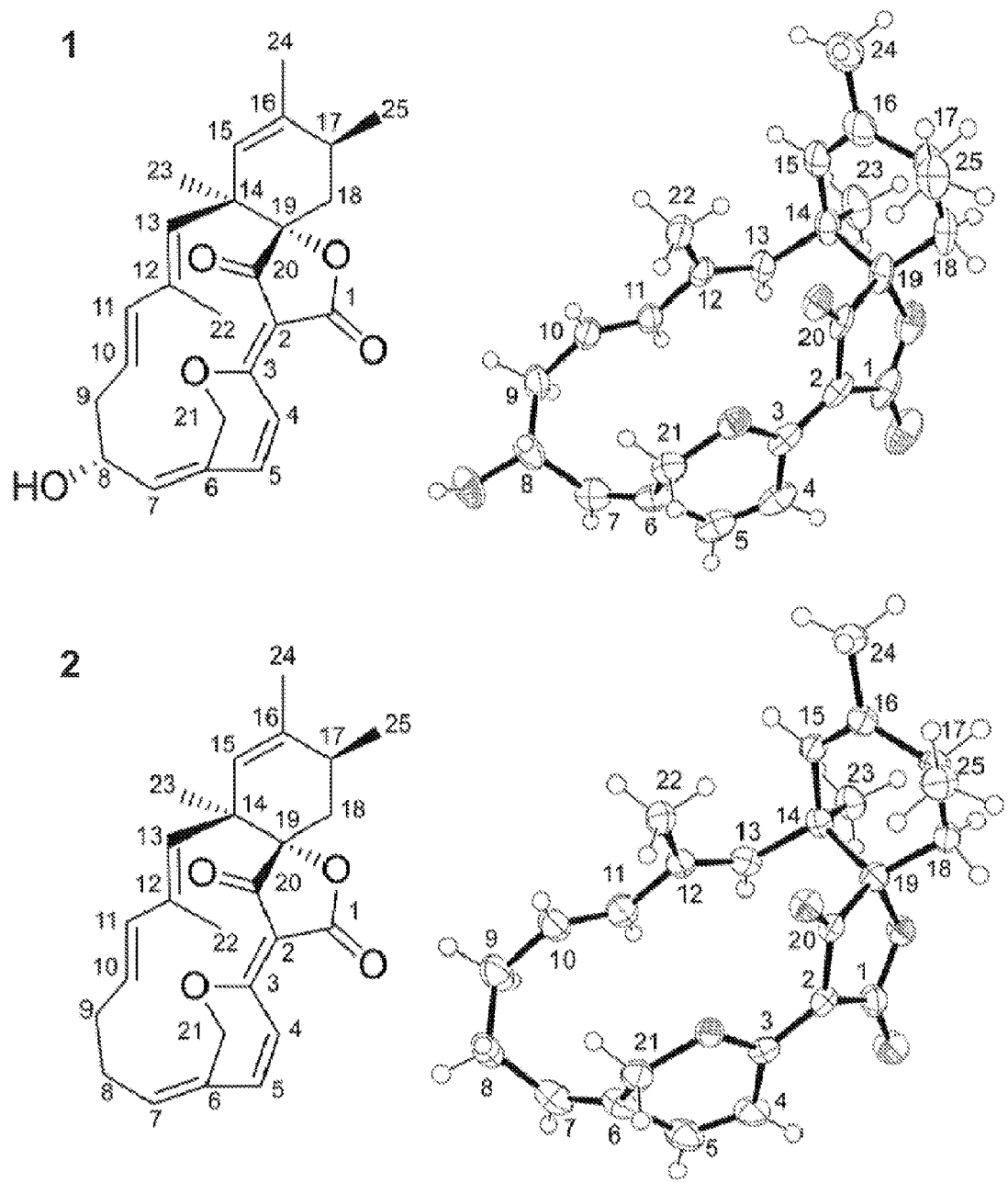
FIG. 2 shows the structures of spirohexenolides A (1) and B (2), and corresponding ORTEP drawings of their X-ray crystal structures with ellipsoids drawn at the 50% probability level. The drawings represent absolute configuration as the Flack x parameter was 0.0(3) (for a definition, see: Flack, Acta Crystallogr, Sect A, 39:876-881 (1983)).

After identification by ¹H NMR and MS analyses, small yellow needles of compound 1 were obtained by perfusion of a chloroform solution of 1 with benzene. Yellow plates were more effectively obtained by recrystallization from ethanol, mp 280-285° C. dec. Samples of these crystals were then evaluated by X-ray crystallography. The structure of 1 was refined to a final R1 of 4.6%. With use of anomalous copper dispersion effects (for an example, see: Niu et al., Org Lett, 9:2437-2440 (2007); for a definition, see: Flack, Acta Crystallogr, Sect A, 39:876-881 (1983)), absolute stereochemical information was obtained as depicted in FIG. 2.

Spectroscopic methods confirmed the crystal structure as follows. A molecular formula for 1 of $C_{25}H_{28}O_5$ was determined from high-resolution EI-MS analysis (m/z 408.1947, M⁺, Δ3.7 ppm). Strong absorption bands at 1754 and 1702 cm⁻¹ in the FT-IR spectrum confirmed the presence of both ester and ketone groups, respectively.

An NMR data set including ¹H, ¹³C, gCOSY, TOCSY, NOESY, ROESY, HMQC, HSQC, DEPT, and HMBC spectra was collected for spirohexenolide A (1) in CDCl₃ (Table 1). Twenty-five resonances were observed in the ¹³C spectrum as expected from the HRMS data. The DEPT spectrum indicated sixteen protonated carbons including four methyl carbons, an oxymethylene, two aliphatic methylene carbons, an aliphatic methine, an oxymethine, and seven olefin methine carbons. Three of the nine quaternary carbons were observed in the olefin region for a total of ten olefinic carbon resonances, indicating five double bonds.

Three of the six remaining quaternary carbons appeared in the carbonyl region of the spectrum, one of which was the conjugated ketone at $\delta_C$ 196.0 and two of which appeared in the ester/lactone region at $\delta_C$ 169.3 and $\delta_C$ 165.7; this was supported by the carbonyl peaks in the FT-IR spectrum. The fourth was thought to be a quaternary center due to its upfield shift at $\delta_C$ 44.3. The two quaternary carbons at $\delta_C$ 100.8 and $\delta_C$ 89.2 remained ambiguous.

Analysis of the ¹H and gCOSY spectra of 1 (FIG. 3a) revealed four spin systems. The first system began with the two downfield olefin methine protons H-4 ($\delta_H$ 7.44, d, 10.0 Hz) and H-5 ($\delta_H$ 7.02, d, 10.0 Hz). H-5 showed allylic coupling to oxymethylene proton H-21a ($\delta_H$ 4.73, d, 12.5 Hz), implicating a four-carbon subunit for this spin system with a junction at quaternary olefinic C-6. The J=10.0 Hz coupling constant between H-4 and H-5 was consistent with a cis-olefin.

The second spin system comprised a linear subunit including olefinic methine H-7 ($\delta_H$ 5.72, d, 8.4 Hz), oxymethine H-8 ($\delta_H$ 4.60, m), aliphatic methylene pair H₂-9 ($\delta_{H-9a}$ 2.60, m, $\delta_{H-9b}$ 2.17, dt, 12.3, 10.6 Hz), olefinic methine H-10 ($\delta_H$ 5.55, ddd, 5.4, 10.6, 15.5 Hz), and olefinic methine H-11 ($\delta_H$ 5.69, d, 15.5 Hz). The J=15.5 Hz coupling constant between H-10 and H-11 established the E configuration for the $\Delta^{10,11}$ olefin. The third spin system was an isolated two-resonance spin system including olefinic methine H-13 ($\delta_H$ 5.07, s) and vinyl methyl H₃-22 ($\delta_H$ 1.76, s), presumably connected via quaternary olefinic C-12.

The fourth spin system was a branched subunit beginning with olefinic methine H-15 ($\delta_H$ 5.29, s), which displayed allylic coupling to vinyl methyl H₃-24 ($\delta_H$ 1.76, s) and to aliphatic methine H-17 ($\delta_H$ 2.39, m). H-17 also coupled to methyl H₃-25 ($\delta_H$ 1.34, d, 7.2 Hz) and methylene pair H₂-18 ($\delta_{H-18a}$ 2.35, m, $\delta_{H-18b}$ 1.71, d, 13.6 Hz). The C-23 methyl group was not in any of the spin systems, indicating that it was attached to a quaternary center.

Figure 3:
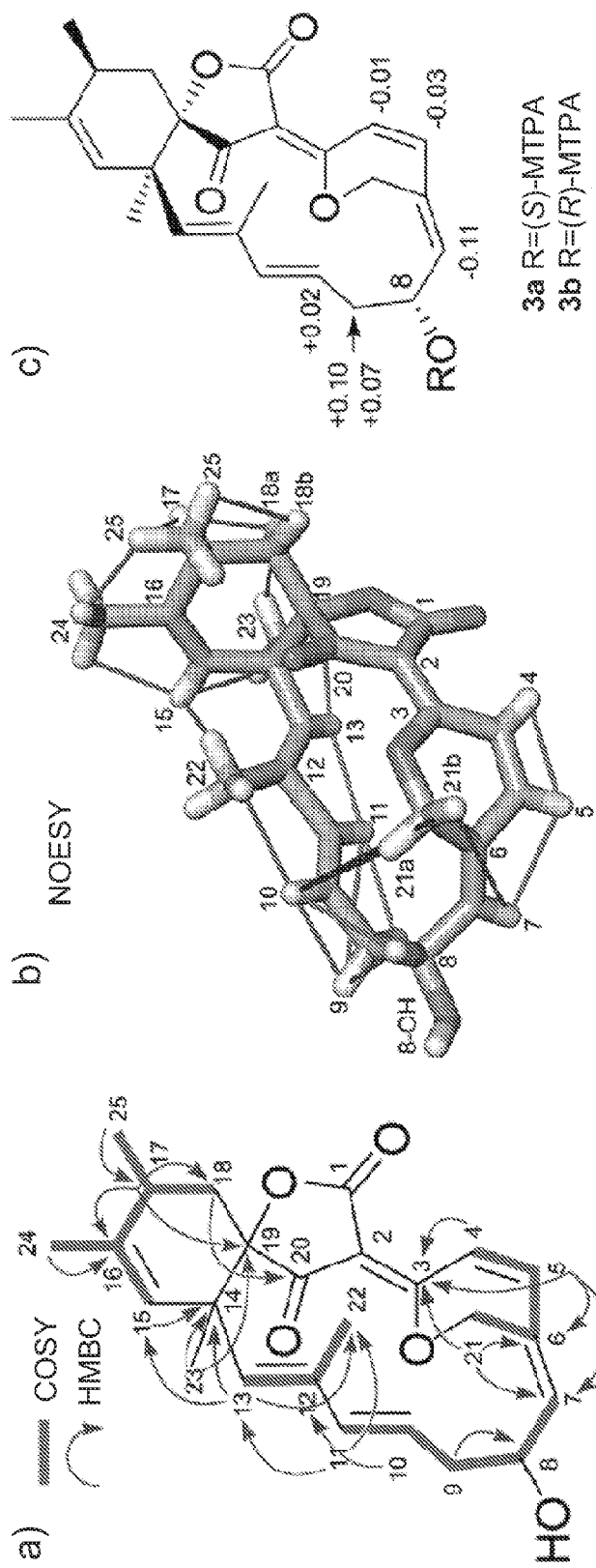
FIG. 3 shows select NMR data. (a) Key gCOSY and HMBC correlations for spirohexenolide A (1) and (b) Nuclear Overhauser effects identified through analysis of a NOESY spectrum as mapped on the X-ray crystal structure of 1. Both proximal (green) and transannluar (blue) NOEs are shown. (c) $\Delta\delta_{S-R}$ values for the Mosher esters 3a and 3b.

FIG. 3a depicts several of the key HMBC correlations that validated the structure. The HMBC data confirmed the assignments of the C-3 and C-6 ¹³C signals at $\delta_C$ 165.7 and $\delta_C$ 126.7, respectively, based on the correlations from H-4, H-5, and H-21a, all in the first spin system. Tethering of the first and second spin systems hinged on the HMBC correlation from H-5 and H-21b to olefinic methine C-7, suggesting quaternary C-6 as the junction. This C-3 to C-11 segment could be extended to include the CH-13/CH₃-22 system based on reciprocal HMBC correlations between olefinic H-11 and H-13 and their respective carbons. Quaternary olefinic C-12 ($\delta_C$ 136.2) was assigned as the link due to correlations from H-10 and H₃-22. Mutual HMBC correlations between olefinic H-13 and H-15 and their respective carbons combined with their additional correlation to the upfield quaternary center C-14 ($\delta_C$ 44.3) indicated that C-14 was the link to the fourth spin system. Correlation from the isolated CH₃-23 methyl group to C-14 established its position. Quaternary C-16 ($\delta_C$ 133.4) was assigned due to HMBC correlations from H-17, H-18b, H₃-24, and H₃-25. Fourth spin system protons H-15, H-17, H₂-18 and the isolated methyl H₃-23 correlated to the downfield quaternary carbon C-19 ($\delta_C$ 89.2), placing it adjacent to CH₂-18, indicating a bond to quaternary C-14 and thus a cyclohexene ring. The ketone carbonyl at C-20 ($\delta_C$ 196.0) was assigned adjacent to C-19 due to correlations from CH₂-18. The chemical shift of C-19 suggested oxidation, which implicated it as the quaternary center of a spirotetronate system due to its inclusion in the cyclohexene ring. C-1 ($\delta_C$ 169.3) and C-2 ($\delta_C$ 100.8) were assigned based on their chemical shifts since no protons were within HMBC correlation distance to them.

The NOESY spectrum (Table 1) revealed an NOE correlation between methylene proton H-18a and the H₃-23 isolated methyl group, providing additional support for the presence of the cyclohexene ring. The transannular NOE correlation between olefinic methine H-10 and oxymethylene H₂-21 was indicative of the macrocycle in 1. Key NOESY interactions are shown in FIG. 3b. Taken together, the NMR data were consistent with the X-ray crystal structure. The absolute configuration of 1 was confirmed by preparing (S)-MTPA (3a) and (R)-MTPA (3b) esters (FIG. 3c) (Dale et al., J Am Chem Soc, 95:512-519 (1973); Ohtani et al., J Am Chem Soc, 113:4092-4096 (1991)).

With structure elucidation studies complete, we returned to culturing to produce additional quantities of compound 1 for biological studies. Using our optimized strains, we screened for media that provided an optimal yield of 1. After evaluating over 50 different liquid cultures, we found that culturing *S. platensis* MJ1A in a fermentation media (6% w/v soluble starch, 1% w/v dry yeast, 1% w/v β-cyclodextrin, 1% w/v CaCO$_3$) containing 2% of Amberlite XAD-16 resin provided 1 at up to 325 mg/L (as discussed in more detail above). By increasing the resin content to 10%, we were able to obtain 15-20 mg/L of a second metabolite spirohexenolide B (2) from these cultures. The structure of 2 was characterized by X-ray crystallography (FIG. 2) and subsequent NMR analyses (Table 2) indicating that 2 failed to undergo oxidation at C-8, suggesting that 2 is a biosynthetic precursor to 1.

Having possession of this isolated natural product made possible the characterization of its biological activity. While we identified 1 using an antibiotic screen, the activity of 1 was more significant in tumor cell lines. Initial activity studies used the human colon tumor HCT-116 cell line, and 1 displayed cytotoxicity activity with a GI$_{50}$ value of 36.0±5.1 μM, using the MTT assay. Submission of 1 to the single and multiple dose screens NCI-60 human tumor cell line screen (Shoemaker, Nat Rev Cancer, 6:813-823 (2006)) identified the enhanced activity as given by lower GI$_{50}$ values in leukemia (CCRF-CEM, MOLT-4, and RPMI-8226), lung cancer (HOP-92), and colon cancer (SW-629) cell lines (complete data provided in the Supporting Information). Subsequent COMPARE analysis failed to provide a match to a known compound and any associated mechanism of action, suggesting a novel anticancer action for 1. In vivo studies in athymic nude mice produced toxicity after a single dose of 1 (6-10 mg/kg), indicating the threshold for further studies.

Figure 4:
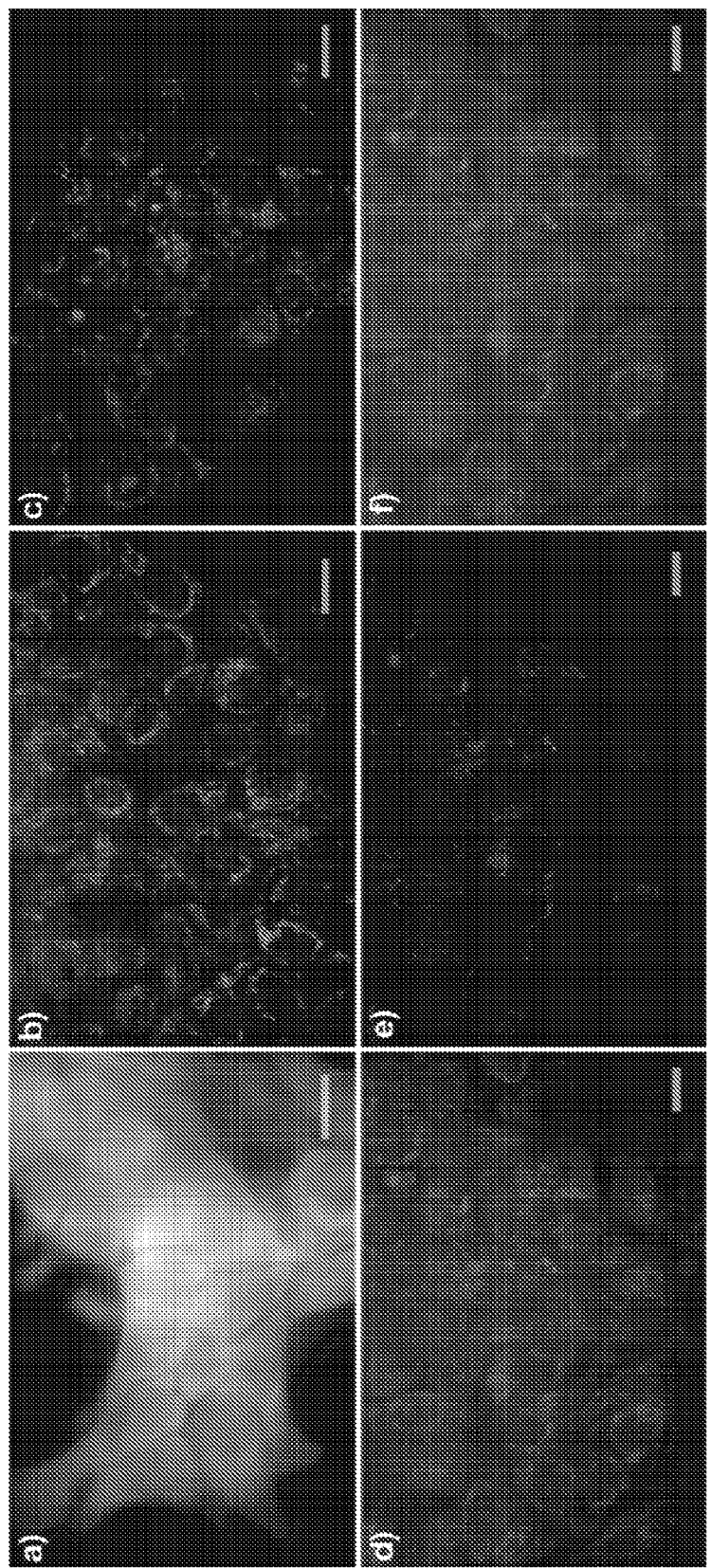
FIG. 4 shows the uptake and subcellular localization of spirohexenolide A (1) in HCT-116 cells. Confocal fluorescent images from HCT-116 cells treated with 10 µM 1 for (a) 1 h, (b) 6 h, and (c) 12 h. Cells were washed twice with media prior to imaging. Live cell images were collected with excitation from a laser at 488 nm (emission filtered at 524±40 nm). Co-staining with LysoTracker Red DND-99 indicates that compound 1 localizes within the lysosomes. HCT-116 cells were treated with 10 µM 1 for 6 h and washed before staining with 10 µM LysoTracker Red DND-99 (Lemieux et al., Anal Biochem, 327:247-251 (2004)) for 20 min. (d) Fluorescence from 1 collected with excitation from a laser at 488 nm (emission filtered at 524±40 nm). (e) Fluorescence from LysoTracker Red DND-99 collected with excitation from a laser at 568 nm (emission filtered at 624±40 nm). (f) Two-color overlap depicting the fluorescence from 1 (red) and LysoTracker Red DND-99 (green). Yellow denotes overlap of both probes. Bars denote 10 µm.
Figure 14:
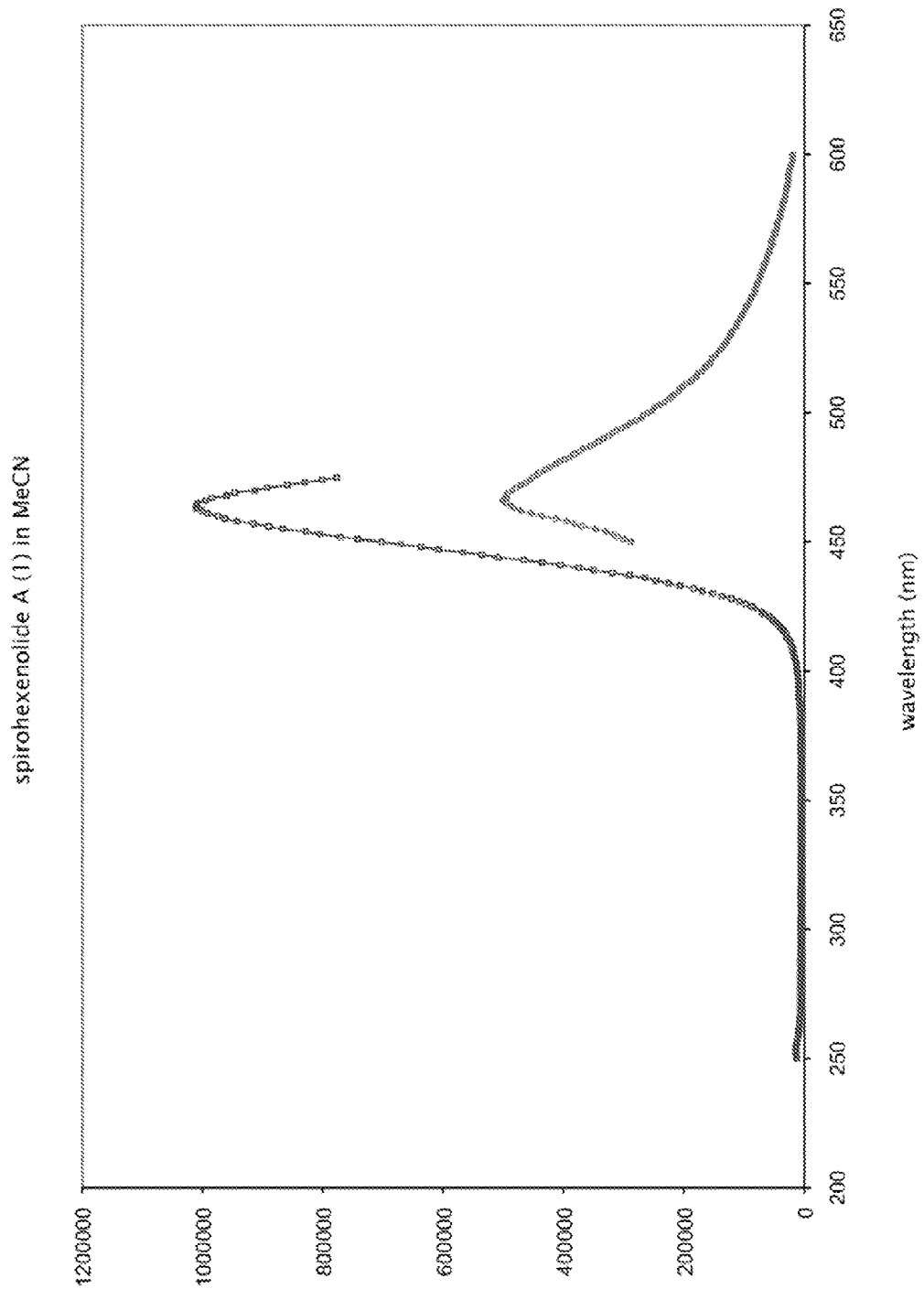
FIGS. 14-15 show fluorescence spectra for spirohexenolide A(1).
Figure 15:
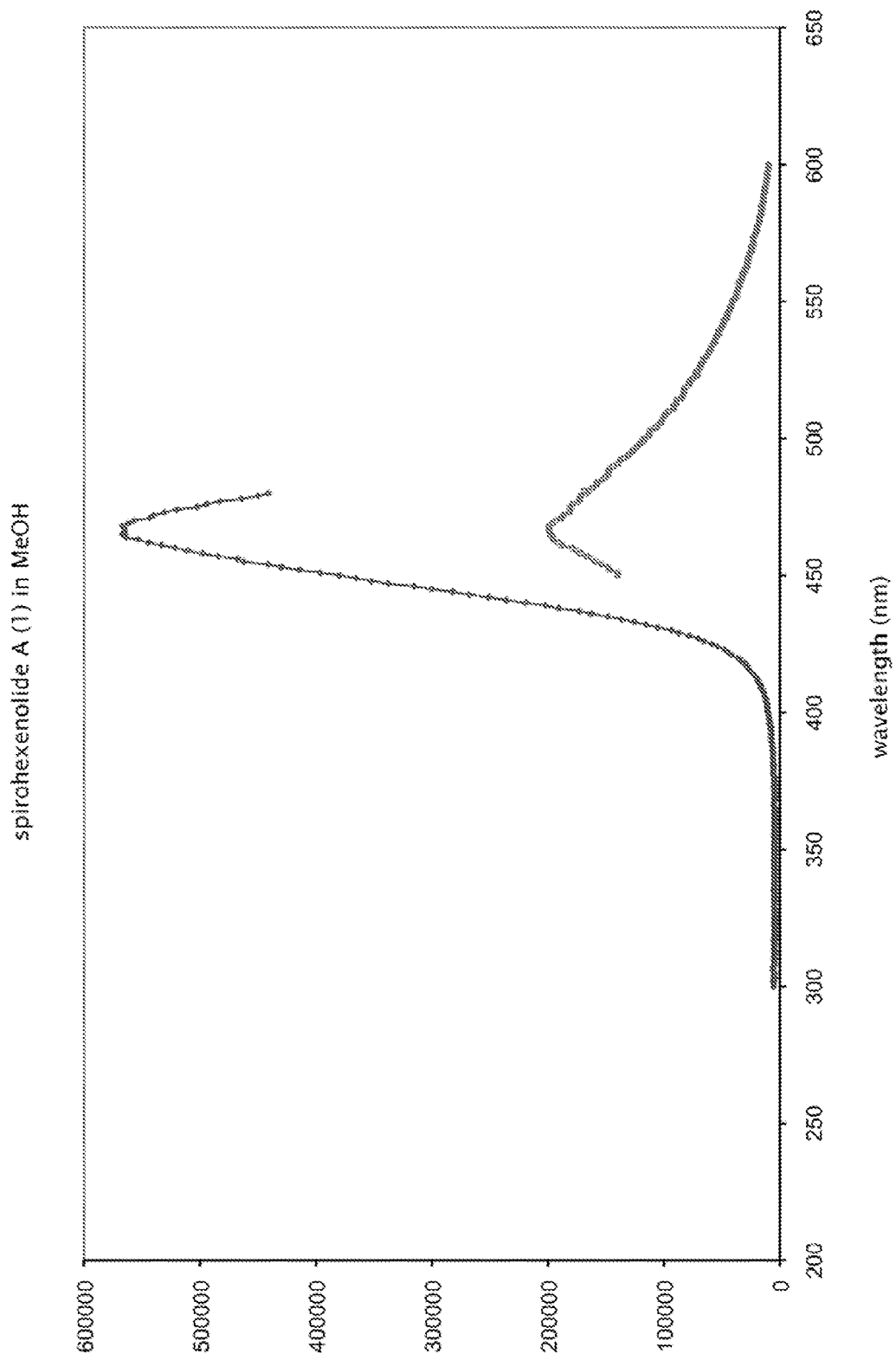

Cellular uptake and localization of 1 in HCT-116 tumor cells was then evaluated using fluorescence microscopy. Fortunately, spirohexenolide A (1) was natively fluorescent, with an excitation maximum $\lambda_{max}$=435 nm and emission maximum at $\lambda_{max}$=466 nm (FIGS. 14 and 15). HCT-116 cells were treated with 10 μM 1 in DMEM containing 10% FCS, 100 U/mL penicillin-G, and 100 μg/mL streptomycin and analyzed by fluorescence microscopy. Spirohexenolide A (1) was readily uptaken and appeared within minutes throughout the cell (FIG. 4a). Within 6-12 h, fluorescence from 1 concentrated within vesicles surrounding the nucleus and remained in these structures (FIG. 4b). This staining could not be washed from the cells by repetitive incubation with media and remained consistent thereafter (FIG. 4c). Co-staining experiments with a panel of organelle probes provided a direct correlation with LysoTracker Red DND-99 (Lemieux et al., Anal Biochem, 327:247-251 (2004)) (FIGS. 4d-4e) indicating that the localization occurred in the lysosomes.

Example 2

Identification of Spirohexenolide A as a Selective Tumor Growth Inhibitor

General.

Column chromatography was performed with EMD Geduran Silica Gel 60 (40-63 mesh). Thin layer chromatography was performed on EMD Silica Gel 60 F254 pre-coated plates. TLC plates were visualized by short wave UV irradiation (254 nm) and then stained with a ceric ammonium molybdate solution. NMR spectra were collected on either a Bruker Avance 800 MHz, Bruker DMX500, Varian VNMRS 500 MHz NMR spectrometer equipped with XSens cold probe, JEOL ECA 500 MHz or Varian Mercury Plus 400 MHz. The FT-IR sample was prepared as a thin film on a KBr disc, and the spectrum was recorded with a Nicolet Magna-IR 550 series II Spectrometer. The mass spectra were collected on a ThermoFinnigan LCQ DECA mass spectrometer or ThermoFinnigan MAT900XL with electron impact ionization. A Thermo Scientific LTQ Orbitrap XL mass spectrometer was used for high-resolution electrospray ionization mass spectrometry analysis (HR-ESI-MS). The optical rotation was measured with a Perkin-Elmer 241 Polarimeter with a 1 dm path length. The melting point was measured on a Thomas Hoover capillary melting point apparatus and is uncorrected. The absorption and emission data were obtained in CH$_3$OH or CH$_3$CN on either a Beckman-Coulter DU 530 or a PTI QuantaMaster spectrophotometer.

Mutagenesis of S. platensis.

Spore suspensions were prepared from strains of S. platensis in glycerol. An 1 μL aliquot of these suspensions were added to 1 mL in sterilized water and further diluted by addition of 10 μL of this solution into 10 mL of water to yield a solution containing approximately 6×10$^5$ spores/mL. This solution was then poured onto a sterile 9 cm glass Petri dish and UV irradiated (Stratalinker 1800) at 8000 μJ at 12 cm distance while being stirred. Samples were taken in every 6 seconds over a 3 min period. After serial dilution of UV-irradiated spore suspension in deionized H$_2$O, the sample was spread onto Bennett's agar (1.0% w/v glucose, 0.2% w/v pancreatic digest of casein, 0.1 w/v of yeast extract, 0.1% w/v beef extract, 1.5% w/v of agar in deionized H$_2$O at pH 7.0), YEMED agar (0.4% w/v yeast extract, 1.0% w/v malt extract, 0.4% w/v glucose, 1.5% w/v agar in deionized H$_2$O at pH 7.2) and ISP4 agar (1.0% w/v soluble starch, 0.2% w/v CaCO$_3$, 0.1% w/v K$_2$HPO$_4$, 0.1% w/v MgSO$_4$.7H$_2$O, 0.1% w/v NaCl, 0.2% w/v (NH$_4$)$_2$SO$_4$, 0.001% w/v FeSO$_4$.7H$_2$O, 0.001% w/v MnCl$_2$.4H$_2$O and 0.001% w/v of ZnSO$_4$.7H$_2$O in deionized H$_2$O at pH 7.2) for examining the morphological differentiating colonies. In order to protect photoreactivation, the plates were wrapped with foil for 24 h and then incubated in the dark at 30° C. for 15 days.

Mutant Screening Identifies Producer Strains S. platensis MJ1A1 and MJ1A2.

After 15 days of incubation, survival colonies were transferred onto R2YE media (10.3% w/v sucrose, 0.5% w/v yeast extract (Difco), 0.01% w/v casaminoacids (Difco), 0.025% w/v K$_2$SO$_4$, 1.01% w/v MgCl$_2$.6H$_2$O, 1% w/v glucose, 0.025% w/v KH$_2$PO$_4$, 0.29% w/v CaCl$_2$.2H$_2$O, 0.0008% w/v ZnCl$_2$, 0.004% w/v FeCl$_3$.6H$_2$O, 0.0004% w/v CuCl$_2$.2H$_2$O, 0.0004% w/v MnCl$_2$.4H$_2$O, 0.0004% w/v Na$_2$B$_4$O$_7$.10H$_2$O, 0.0004% w/v (NH$_4$)$_5$Mo$_7$O$_{24}$.4H$_2$O 0.3% w/v L-proline, 0.573% w/v N-tris(hydroxymethyl)methyl-2-aminoethane-sulfonic acid (TES), 0.005% v/v 1 N NaOH to provide a pH 7.2). Once the mutants were sporulated, agar cones (3 mm OD×5 mm height) were excised containing a single colony and stamped on top of a glucose basal salt (1% g of glucose, 0.01% yeast extract, 1.5% agar, 0.02% MgSO$_4$.7H$_2$O, 0.001% NaCl, 0.001% FeSO$_4$.7H$_2$O, 0.001% MnSO$_4$.4H$_2$O 0.2% NH$_4$Cl, 0.465% K$_2$HPO$_4$ 0.09% of KH$_2$PO$_4$ at pH 7.0) agar seeded with ~8×10$^7$ of Bacillus subtilis 6633 per cm$^2$. After incubation at 37° C. for 24 h, colonies showing a zone of inhibition were compared against their parent strain. Using this method, strains MJ1A, MJ2B and MJ6 (FIG. 1a) were obtained.

Optimized Culturing of Spirohexenolide A (1) from S. platensis Strain MJ1A1.

A single colony of S. platensis MJ1A1 grown on YEMED agar was resuspended in 50 μl of sterilized water using a sterilized pellet pestle and inoculated into 3 mL of TSB broth (BD bioscience) and shaken at 220 rpm at 28° C. for 40 hours. An aliquot (2 mL) of this starter culture was transferred into a 250 mL baffled Erlenmeyer flask containing 100 mL of seed medium containing 1% w/v glucose, 2.4% w/v soluble starch, 0.3% w/v beef extract, 0.5% w/v tryptone, 0.5% w/v yeast extract and 2.0% w/v $CaCO_3$ adjusted to pH 7.2. After shaking the seed medium for 48 h at 220 rpm and 28° C., a 50 ml aliquot was transferred to 2.8 L baffled Erlenmeyer flask containing 500 ml of fermentation media (6% w/v soluble starch, 1% w/v dry yeast, 1% w/v (3-cyclodextrin, 0.2% w/v $CaCO_3$ adjusted to pH 6.8 prior to sterilization) and 2% w/v of Amberlite XAD-16 resin (Alfa Aesar) that was washed repetitively with deionized water prior to sterilization. The fermentation media was shaken for 72 h at in 220 rpm at 28° C.

Extraction.

When cultured without Amberlite XAD-16 resin, samples of culture were centrifuged for 20 min at 4,500 rpm to separate supernatant from precipitates. The supernatant was collected and shaken with an equal volume of EtOAc in baffled Erlenmeyer flask for 2 h on a rotary shaker. The EtOAc was collected and concentrated by rotary evaporation to provide the crude extract. When cultured in the presence of Amberlite XAD-16 resin, cultures were filtered through cheesecloth to collect the resin. The resin was then returned to the baffled flask and acetone (250 mL) and EtOAc (250 mL) were added. The flask was shaken for 2 h at 220 rpm. The resin was filtered again through cheesecloth, and the filtrate was concentrated on a rotary evaporator until only insoluble solids and water remained. EtOAc was added until most of the solids were dissolved, and the mixture was poured into a reparatory funnel. The aqueous layer was extracted with additional EtOAc (2×100 mL), and the combined organic layers were concentrated.

NMR Guided Fractionation.

Samples of the crude extracts from cultures of *S. platensis* MJ1A, MJ1A1 or MJ1A2 were dissolved in 50-100 mL of 1:1 hexanes:EtOAc (sonication was used to facilitate dissolution). A 2 in. ID column containing silica gel (EM Sciences) was packed with 1:1 hexanes:EtOAc, and then the solutions of the samples were loaded. The column was run with 1:1 hexanes:EtOAc for at least two column volumes before EtOAc (100%) was used to elute 1., $R_f$=0.29, EtOAc (100%). Compound 1 could be visualized by ceric ammonium molybdate, 2,4-dinitrophenylhydrazine, iodine, and potassium permanganate stains, and short wave UV (excitation at 254 nm). Pure spirohexenolide A (1) was obtained after a second Flash column using a gradient from hexanes to EtOAc or trituration with small amounts of absolute ethanol. Spirohexenolide A (1) displayed an $[\alpha]_D^{25}$=+551.3 (c=0.4, $CHCl_3$) and melted at 285° C. (uncorrected). Key IR absorbances were observed at 3469, 1754, and 1702 $cm^{-1}$. Spirohexenolide A (1) was fluorescent with an absorption maxima at $\lambda_{max}$=242 ($\epsilon$=21,090 $cm^{-1}$ $M^{-1}$) and 343 nm ($\epsilon$=8,358 $cm^{-1}$ $M^{-1}$) and emission maxima at $\lambda_{max}$=475 nm in $CH_3OH$. NMR data for 1 is provided in Table 3. Copies of select spectra are provided within the Supporting Information.

TABLE 3

$^1H$, $^{13}C$, gCOSY, NOESY and HMBC NMR data for spirohexenolide A (1) in $CDCl_3$.

| position | $^1H$ δ (J in Hz)[a] | $^{13}C$ δ (type)[b] | COSY[c] | NOESY[c] | HMBC[c] |
|---|---|---|---|---|---|
| 1 |  | 169.3 (C) |  |  |  |
| 2 |  | 100.8 (C) |  |  |  |
| 3 |  | 165.7 (C) |  |  |  |
| 4 | 7.44 d (10.0) | 120.3 (CH) | 5 | 5 | 3, 6 |
| 5 | 7.02 d (10.0, <1) | 142.1 (CH) | 4, 21a | 4, 7 | 3, 6, 7, 21 |
| 6 |  | 126.7 (C) |  |  |  |
| 7 | 5.72 d (8.4) | 139.3 (CH) | 8 | 5, 21b | 5, 21 |
| 8 | 4.60 m | 69.3 (CH) | 7, 9a, 9b | 9a, 9b, 10 | 9 |
| 9a | 2.60 m | 42.6 ($CH_2$) | 8, 9b, 10 | 8, 9b, 10, 11[e] | 8, 10, 11 |
| 9b | 2.17 dt (10.6, 12.3) |  | 8, 9a, 10 | 8, 9a, 10, 11 | 8, 10, 11 |
| 10 | 5.55 ddd (5.4, 10.6, 15.5) | 120.8 (CH) | 9a, 9b, 11 | 8[d], 9a, 9b, 13[e], 21a, 21b[d], 22[d] | 9, 11, 12 |
| 11 | 5.69 d (15.5) | 140.9 (CH) | 9a, 10 | 9b, 13, 22[d] | 9, 10, 13, 22 |
| 12 |  | 136.2 (C) |  |  |  |
| 13 | 5.07 s | 134.8 (CH) | 22 | 10, 11, 15[e], 23[e] | 11, 14, 15, 22, 23 |
| 14 |  | 44.3 (C) |  |  |  |
| 15 | 5.29 s | 128.0 (CH) | 17, 24 | 13, 23, 24 | 13, 14, 17, 19, 24 |
| 16 |  | 133.4 (C) |  |  |  |
| 17 | 2.39 m | 33.5 (CH) | 15, 18a, 18b, 25 | 18a, 25 | 15, 16, 18, 19, 25 |
| 18a | 2.35 m | 33.3 ($CH_2$) | 17, 18b | 17, 18b, 23 | 14, 17, 19, 20, 25 |
| 18b | 1.71 d (13.6) |  | 17, 18a | 18a, 25 | 14, 16, 17, 19, 20, 25 |
| 19 |  | 89.2 (C) |  |  |  |
| 20 |  | 196.0 (C) |  |  |  |
| 21a | 4.73 d (12.5) | 64.8 ($CH_2$) | 5, 21b | 10, 21b[d] | 3, 5, 6, 7 |
| 21b | 4.57 d (12.5) |  | 21a | 7, 10, 21a | 5, 6, 7 |
| 22 | 1.76 s | 14.1 ($CH_3$) | 13 | 10, 11 | 11, 12 |
| 23 | 1.19 s | 27.2 ($CH_3$) |  | 13, 15, 18a | 13, 14, 15, 19 |
| 24 | 1.76 s | 22.0 ($CH_3$) | 15 | 15, 25 | 15, 16, 17, 18 |
| 25 | 1.34 d (7.2) | 19.6 ($CH_3$) | 17 | 17, 18b, 24[d] | 16, 17, 18 |

[a]$^1$H-NMR data was collected at 500 MHz.
[b]$^{13}$C NMR data was collected at 100 MHz. Assignments confirmed by evaluation of the gHMQC and HSQC spectra.
$^{13}$C NMR multiplicities were determined by the $^{13}$C DEPT spectrum.
[b]gCOSY, HMBC, and NOESY spectra were collected at 800 MHz.
[c]HMBC data was reported from $^1$H to $^{13}$C.
[d]Overlapping signals detected.
[e]A weak crosspeak was detected. All spectra were collected at 23° C. in $CDCl_3$.

Synthesis of Mosher Esters 2a and 2b.

The (S)- and (R)-MTPA derivatives 2a and 2b were prepared using a slight modification of the standard procedure (Dale et al., J Am Chem Soc, 95:512-519 (1973); Ohtani et al., J Am Chem Soc, 113:4092-4096 (1991)). (S)-MTPA ester 2a: To a sample of compound 1 (30.3 mg, 0.0743 mmol) in a dry 25 mL round bottom flask with a teflon-coated magnetic stirbar, were added a few crystals of 4-dimethylaminopyridine and the flask was sealed with a rubber septum and flushed with argon. $CH_2Cl_2$ (3 mL), and pyridine (0.120 mL, 1.5 mmol) were added at room temperature, and the mixture was stirred until a yellow solution was achieved. Stirring was then continued as 70 µL of (R)-MTPA-Cl (0.374 mmol) was added via syringe at room temperature. After 30 minutes the solution turned dark green. After 50 min, TLC indicated a new compound had formed ($R_f$=0.76, EtOAc), and that compound 1 had been consumed. The reaction mixture was then poured into a reparatory funnel containing half-saturated $NaHCO_3$ (30 mL), and $CH_2Cl_2$ (20 mL), and the organic layer became yellow again upon shaking. The aqueous layer was extracted with another 20 mL of $CH_2Cl_2$ and the combined organic layers were dried over $Na_2SO_4$ and concentrated under reduced pressure. The residue was dissolved in 3:1 Hexanes:EtOAc (5 mL), and standard flash chromatography with 3:1 Hexanes:EtOAc provided pure 2a (16.3 mg, 35%). See supporting information for $^1H$ and $^{13}C$ NMR spectra of 2a and 2b. The same procedure was used on 1 and (S)-MTPA-Cl to make the (R)-MTPA ester 2b (13.5 mg, 40%). Mass spectral analysis was done on 2b, ESI-MS m/z: 625.18 $[M+H]^+$, 647.21 $[M+Na]^+$; HR-ESI-FT-MS (Orbit-trap-MS) m/z calcd for $C_{35}H_{36}F_3O_7$ $[M+H]^+$625.2408, found 625.2419.

Uptake and Localization Uptake and Localization in HeLa Cells:

HCT-116 cells (ATCC CCL-247) were cultured in Dulbecco's modification of Eagle's medium (DMEM) with 4.5 g $L^{-1}$ glucose, 4.5 g $L^{-1}$ L-glutamine and 5% heat inactivated fetal calf serum (FCS) in glass-bottom dishes. Fluorescent images were collected on a Leica (Wetzlar, Germany) DMI6000 inverted confocal microscope with a Yokogawa (Tokyo, Japan) spinning disk confocal head, Orca ER High Resolution B&W Cooled CCD camera (6.45 µm/pixel at 1×) (Hamamatsu, Sewickley, Pa.), Plan Apochromat 40×/1.25 na and 63×/1.4 na objective, and a Melles Griot (Carlsbad, Calif.) Argon/Krypton 100 mW air-cooled laser for 488, 568, and 647 nm excitations. Confocal z-stacks were acquired in all experiments. The images in FIGS. 7a-7b were collected with excitation filtered at 488 nm with emission at 524±40 nm. Image in FIG. 7c was collected with fluorescence from DNA by staining with SYTO-60 (excitation at 647 nm and emission at 692±40 nm), actin with FITC-phalloidin (excitation at 488 nm and emission at 524±40 nm), and microtubules with BODIPY 564/570 paclitaxel (excitation at 568 nm and emission at 593±40 nm).

X-Ray Crystallography.

A yellow needle 0.25×0.10×0.10 mm in size was mounted on a Cryoloop with Paratone oil. Data were collected in a nitrogen gas stream at 100(2) K using phi and omega scans. Crystal-to-detector distance was 50 mm and exposure time was 10 seconds per frame using a scan width of 0.5°. Data collection was 99.3% complete to 67.00° in θ. A total of 7195 reflections were collected covering the indices, −8<=h<=8, −15<=k<=14, −13<=l<=13. 3065 reflections were found to be symmetry independent, with a Rint of 0.0366. Indexing and unit cell refinement indicated a primitive, monoclinic lattice. The space group was found to be P2(1) (No. 4). The data were integrated using the Bruker SAINT software program and scaled using the SADABS software program. Solution by direct methods (SIR-2004) produced a complete heavy-atom phasing model consistent with the proposed structure. All non-hydrogen atoms were refined anisotropically by full-matrix least squares (SHELXL-97). All hydrogen atoms were placed using a riding model. Their positions were constrained relative to their parent atom using the appropriate HFIX command in SHELXL-97.

The study began by evaluating a panel of S. platensis strains. To guide this effort, we chose an antibiotic screen using the inhibition of Bacillus subtilis 6633 growth as an endpoint. A number of mutant screening approaches were evaluated at the onset of this program and an antibiotic assay using B. subtilis was eventually chosen. This assay was particularly relevant to the discovery of a spirotetronate natural product, as prior studies have shown (Schindler et al., Eur J Biochem, 39:591-600 (1973); Gary et al., J Bacteriol, 64:501-512 (1952); Sundaram et al., Biochim Biophys Acta, 192: 355-357 (1969)). While 1 was initially identified using an antibiotic screen, the biological activity of 1 in tumor cell lines was identified as a unique feature of the material. By applying cycles of UV exposure and selection of spores from a panel of S. platensis strains acquired from various culture collections, we identified three mutant strains, MJ1A (1A, FIG. 1a), MJ2B (2B, FIG. 1a), and MJ6 (6, FIG. 1a) that displayed an increased zone of inhibition over their parent (wt, FIG. 1a). Subsequent efforts (Kieser et al., Practical Streptomyces Genetics, 102-103 (2000)) led to the production of two stable morphologies of MJ1A noted as strains MJ1A1 and MJ1A2. 16S rRNA gene sequence data indicated that MJ1A strain showed high sequence identity to S. platensis NBRC12901 (99%), S. hygroscopicus subsp. glebosus LMG 19950 (99%), S. libani subsp. rufus NBRC 15424 (99%), and S. caniferus NBRC 15389 (99%). Based on this evidence, the assignment of MJ1A1 and MJ1A2 as S. platensis was validated.

$^1$H-NMR guided fractionation was then applied on extracts from cultures of the S. platensis MJ1A1 and S. platensis MJ1A2 (see further details above). Metabolite 1 was identified with a unique signature of olefinic protons in the ethyl acetate (EtOAc) fraction from both cultures. TLC analysis indicated that metabolite 1 (lane 1, FIG. 1b) was readily produced in both strains MJ1A1 (lane 2, FIG. 1b) and MJ1A2 (lane 3, FIG. 1b), as compared to their parent (lane 4, FIG. 1b). Control experimentation indicated that 1 also did not appear in two homologies of FERM BP-8442 (lanes 5-6, FIG. 1b).

After identification by $^1$H-NMR and MS analyses, small yellow needles of 1 were obtained by perfusion of chloroform with benzene. Later, it was discovered that yellow needles and plates were more effectively obtained by recrystallization from ethanol, mp=285° C. (dec). Samples of these crystals were then evaluated by X-ray crystallography. The structure of 1 was refined to a final R1 of 4.6%. Using anomalous copper dispersion effects, we were able to obtain absolute stereochemical information as depicted in FIG. 2. We named this material spirohexenolide A (1).

Spectroscopic methods were then applied to confirm the crystal structure. A molecular formula for 1 was determined to be $C_{25}H_{28}O_5$ from high resolution ELMS analysis [m/z=408.1947, [M]$^+$, Δ3.7 ppm]. This formula matched that obtained by X-ray analysis. The FT-IR spectrum was also in agreement with the crystal structure, confirming the presence of both ester and ketone functional groups with strong absorption bands at 1754 cm$^{-1}$ and 1702 cm$^{-1}$, respectively.

Figure 5:
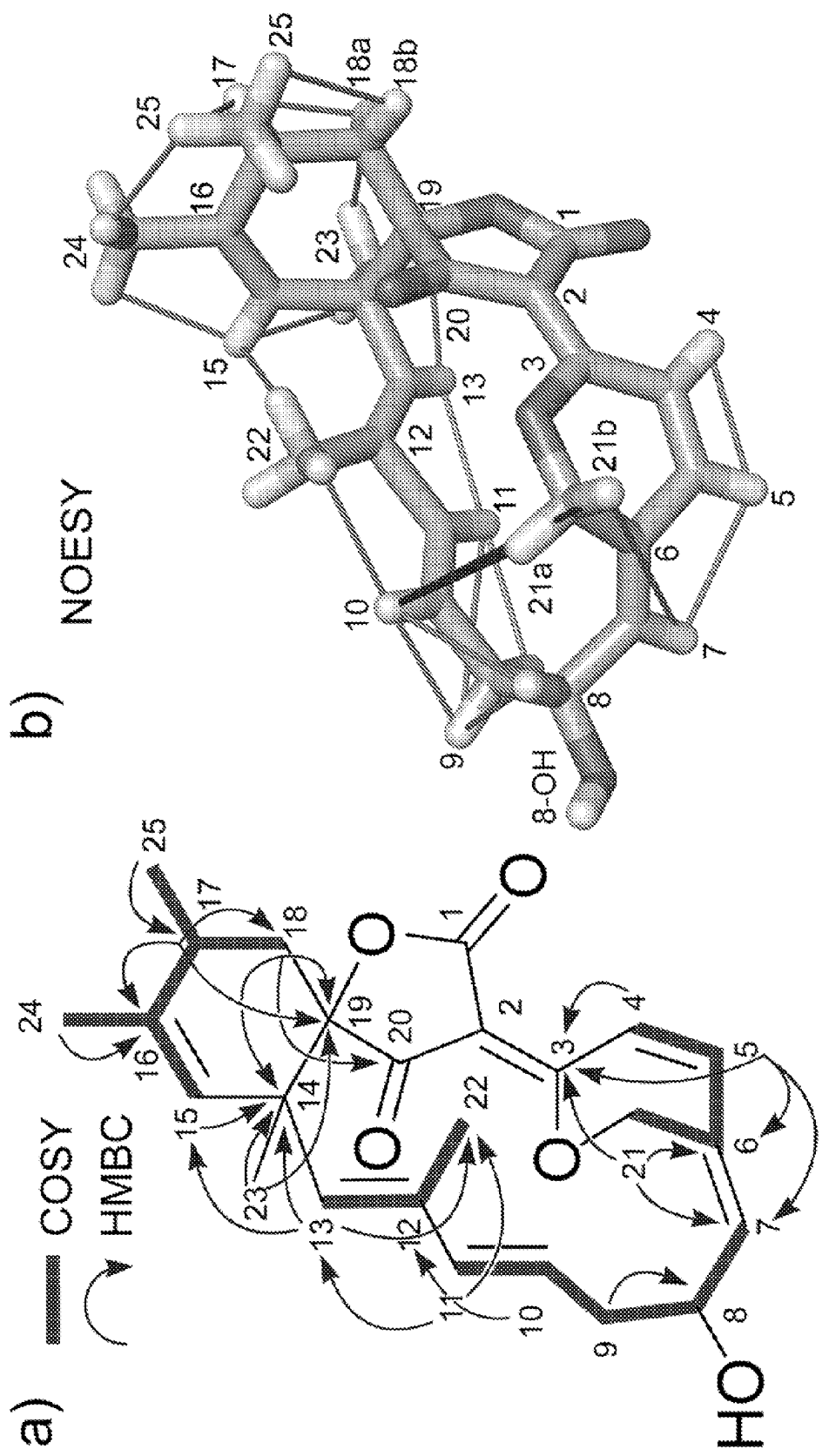
FIG. 5 shows select NMR data. a) Key gCOSY and HMBC correlations in spirohexenolide A (1) and b) Nuclear overhauser effects identified through analysis of a NOESY spectrum as mapped on the X-ray crystal structure of 1. Both proximal (green) and transannluar (blue) NOEs are shown.

Turning to NMR analysis, a data set including $^1$H, $^{13}$C, gCOSY, TOCSY, NOESY, ROESY, HMQC, HSQC$^{13}$C DEPT, and HMBC spectra was collected on spirohexenolide A (1) in CDCl$_3$ (Table 3). Analysis of the $^1$H and gCOSY spectra of 1 (the COSY spin systems are depicted in FIG. 5a) indicated that the most downfield system contained two doublets from protons at C-4 and C-5. The proton at C-5 showed a weak allylic coupling to one of the protons at C-21, implicating a four-carbon subunit for this spin system with a junction at olefin carbon C-6. The J=10.0 Hz coupling constant between the doublets at C-4 and C-5 was consistent with a cis-olefin.

The next spin system comprised a five-carbon linear subunit composed of the olefinic proton at C-7, the oxymethine at C-8, the methylene pair at C-9, the olefinic proton at C-10, and the olefinic proton doublet at C-11 (FIG. 5a). Analysis of this system indicated that the disubstituted olefin at C-10 and C-11 was trans, due to its large J=15.5 Hz coupling constant. The third spin system was an isolated two-resonance spin system. The olefinic proton at C-13 showed a single cross-peak for the allylic coupling to the methyl group at C-22, presumably connected via the olefin carbon C-12. The final spin system apparent in the gCOSY spectrum was a six carbon subunit. This system began with C-15, which connects via allylic coupling to the methyl group at C-24 and the methine multiplet at C-17. The multiplet at C-17 was coupled to the methyl doublet C-25 and the methylene pair at C-18. The C-23 methyl group was not in any of the spin systems, indicating that it was attached to a fully-substituted carbon. The TOCSY spectrum (see Supporting Information) further confirmed the four spin systems observed in the gCOSY spectrum.

We then collected a NOESY spectrum (Table 3) to compare the interactions to those predicted from our crystal structure (FIG. 2). A 3D projection depicting these interactions is provided in FIG. 5b. The NOE observed between one of the protons at C-18 and the C-23 isolated methyl group provided support for the presence of the cyclohexene ring. In addition, the presence of a transannular NOE between the proton at C-10 and those on C-21 was indicative of the macrolide in 1. Comparison with the X-ray structure showed that each of the observed interactions were within 4.5 Å. The majority of these interactions were under 3.6 Å with four longer range interactions appearing between one proton on C-21 and the protons on C-7 and C-10.

We then turned to evaluate the carbon spectrum. A $^{13}$C DEPT spectrum indicated four methyl carbons, an oxymethylene, two upfield methylene carbons, an upfield methine, an oxymethine, and seven olefin methine carbons. A total of sixteen carbons were protonated, leaving nine fully-substituted carbons. The gHMQC spectrum correlated both of the downfield doublets at C-4 and C-5 and the five olefinic protons present between δ 5.00-5.75 ppm to seven of the ten carbon signals between δ 120-143 ppm. Taken together, these data indicated total of five double bonds. As in the crystal structure, three of them were trisubstituted, since the olefin carbon resonances at δ 136.2, 133.4, and 126.7 ppm were fully-substituted.

Three of the six remaining fully-substituted carbons appeared in the carbonyl region of the spectrum, one of which was the conjugated ketone at δ 196.0 ppm and two of which appeared in the ester/lactone region at δ 169.3 and δ 165.7 ppm. This was supported by the carbonyl peaks in the FT-IR spectrum. The fourth was thought to be a quaternary center due to its upfield shift at δ 44.3 ppm. All but two of the fully-substituted carbons at δ 100.8 and δ 89.2 ppm were assigned and the complete carbon skeleton was established by analyzing the HMBC spectrum (Table 3).

FIG. 5a depicts several of the key HMBC correlations that were instrumental in validating the structure. First, the HMBC data confirmed the assignment of the C-3 carbon at δ 165.7 ppm, based on the correlations to the protons at C-4, C-5, and C-21. Second, the C-6 carbon was assigned by correlation to the same protons. Tethering of the first and second spin systems hinged on the HMBC correlation between the olefinic methine proton at C-5 and the olefinic methine carbon at C-7, suggesting C-6 as the linker. Attachment of the second spin system to the isolated C-13/C-22 system was shown by mutual HMBC correlation between the olefinic protons at C-11 and C-13 and their respective carbons. C-12 was assigned as the link due to HMBC from the C-10 proton and the C-22 methyl group. Correlation from the C-13 olefinic proton to the C-15 carbon established the link from the third system to the final system. C-14 (δ 44.3 ppm) was determined to be the upfield quaternary center, due its correlation to the olefinic protons at C-13 and C-15. Correlation from the isolated C-23 methyl group to C-14 established its position. Carbon C-16 was assigned by HMBC correlation to protons at C-17, C-18, C-24 and C-25. HMBC correlations of protons in the fourth spin system to carbon C-19 (δ 89.2 ppm) placed it adjacent to C-18, while the ketone carbonyl at C-20 correlated only to the C-18 methylene pair. Two carbons had no HMBC correlation, the still ambiguous quaternary carbons at δ 100.8 ppm and one of the lactone carbonyl at δ 169.3 ppm.

Figure 7:
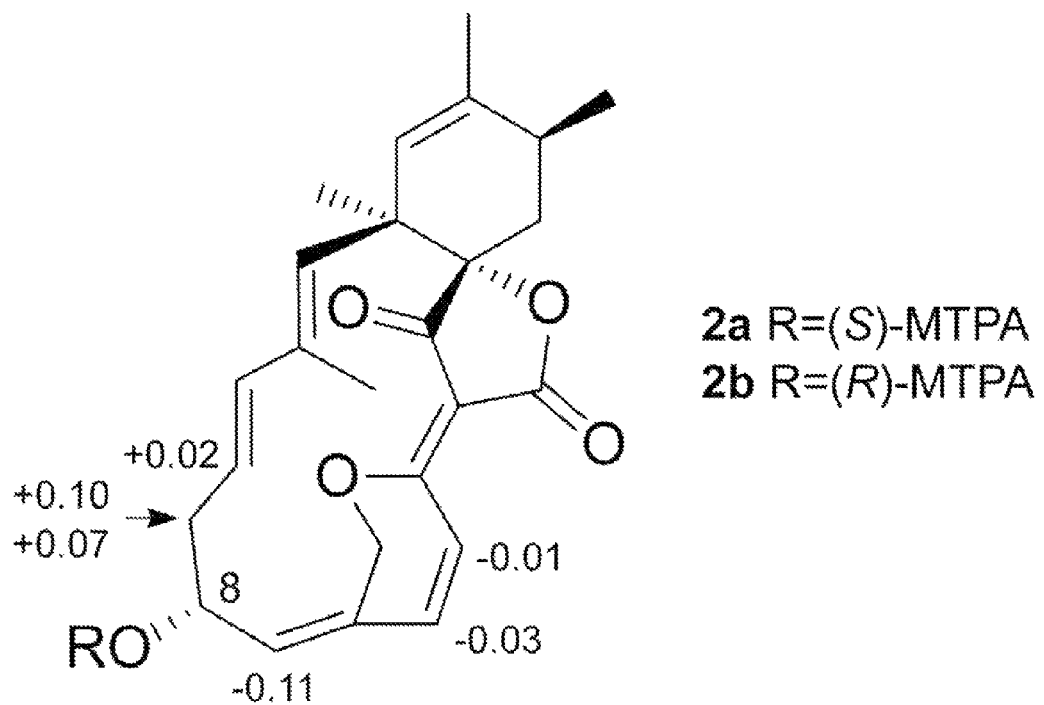
FIG. 7 shows $\Delta\delta S$—R values for the Mosher esters 2a and 2b.

Because the two relatively upfield quaternary centers C-14 and C-19 were assigned six carbons apart in the linear sequence, a bond between the two would be reasonable, and the shift of C-19 (δ 89.2 ppm) indicates oxygenation, which would lead to the spirotetronate structure obtained from X-ray crystallography. In support of this moiety, a HMBC correlation was observed between the C-23 isolated methyl group and the C-19 quaternary center was observed, as well as correlation from the methylene pair at C-18 on the cyclohexene ring to the C-14 quaternary center. This would place the downfield lactone carbon at 169.3 ppm as C-1 as well as explain the chemical shifts at C-2 and C-3. Taken together, the collected NMR data was in support of the X-ray crystal structure. We confirmed the absolute stereochemistry by preparing (S)-MTPA (2a) and (R)-MTPA (2b) esters (FIG. 7).

With structure elucidation studies complete, we returned to culturing to produce additional quantities of 1 for biological studies. After screening media, we found that culturing *S. platensis* MJ1A in a different liquid media containing 2% of Amberlite XAD-16 resin allowed production of 1 at up to 325 mg/L. With access to the natural product, we were now able to characterize its biological activity.

Initial activity studies of 1 used the human colon tumor HCT-116 cell line with cytotoxicity activity at an $IC_{50}$ value of 0.5 µM. Submission of 1 to the single dose NCI-60 human tumor cell line screen (Shoemaker, Nat Rev Cancer, 6:813-823 (2006)) showed selective activity for specific tumor cell lines when dosed at 10 µM, including melanoma, prostate, and renal cancers with 96%, 85, and 95% inhibition, respectively (copies of NCI-60 screening data provided in the Supporting Information). Additional dose-response assays indicated that leukemia, renal cancer, and melanoma cell lines show selective sensitivity to compound 1. Subsequent COMPARE analysis failed to provide a direct link, suggesting a novel mechanism of action. In vivo studies in athymic nude mice indicated toxicity after a single dose over 6-10 mg/kg, indicating the window for further in vivo applications.

Figure 6:
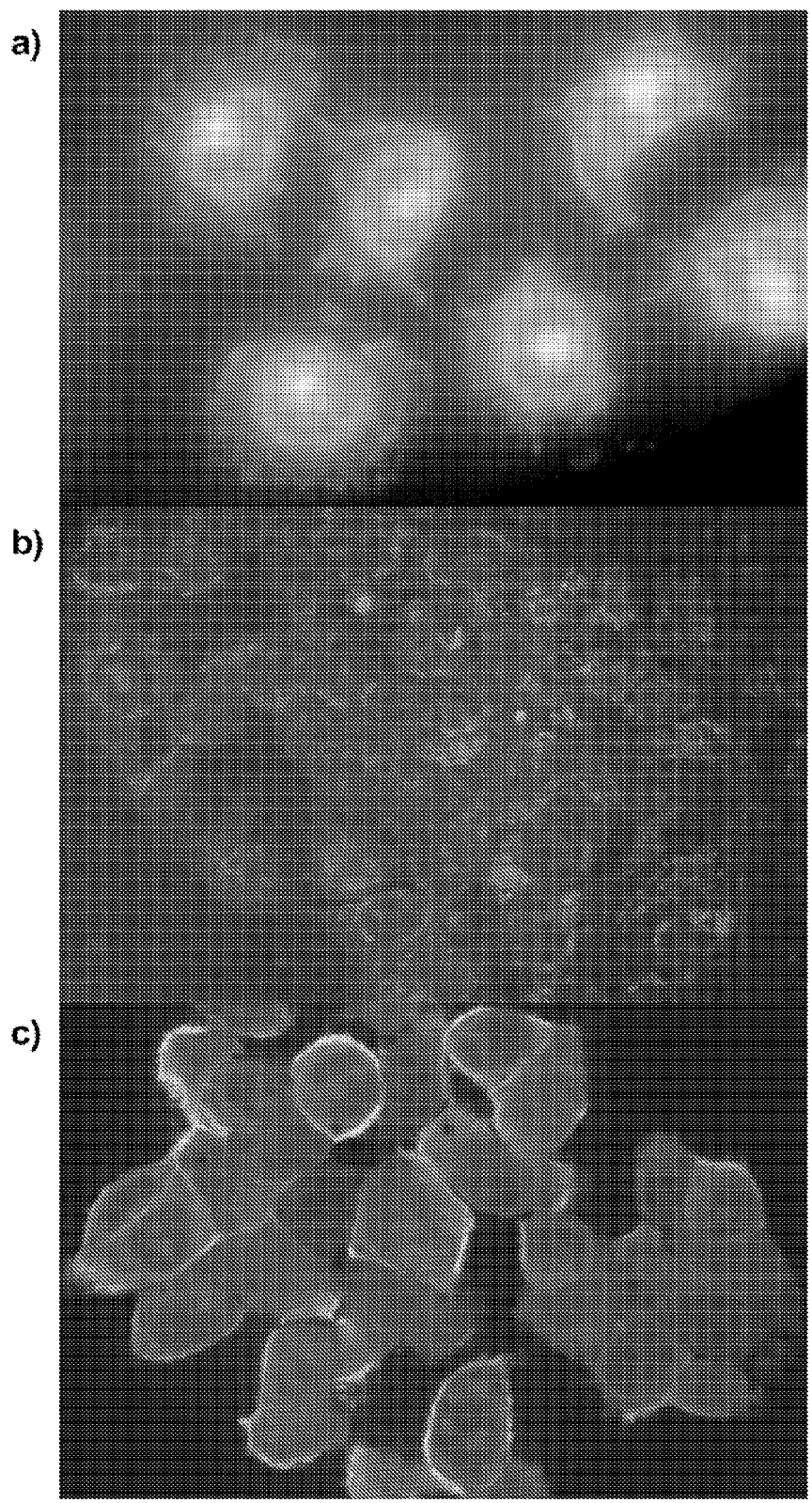
FIG. 6 shows the effects of spirohexenolide A (1) on HCT-116 cells. a) A fluorescent image depicting the phenotypic outcome of HCT-116 cells treated with 10 µM 1 for 12 h. b) A confocal fluorescent image of cells treated as in a) noting the intracellular localization of 1. Images in a) and b) depict live cells. c) A confocal fluorescent image indicating the effects of 1 has on the cell structure. Cells treated as in a) were fixed with 0.1% formalin and stained for their DNA content with SYTO-60 (false colored in blue) (Wlodkowic et al., Cytometry A, 73:496-507 (2008)), actin with FITC-phalloidin (green) (Verderame et al., Proc Natl Acad Sci USA, 77:6624-6628 (1980)), and microtubules with BODIPY FL-paclitaxel (red) (Bicamumpaka et al., Int J Mol Med, 2:161-165 (1998)). For each experiment, HCT-116 cells were cultured to $10^6$ cells/cm$^2$ in a 35 mm poly-D-lysine coated glass-bottom dish and treated with 1 mL of 10 µM 1 in Dulbecco's modified essential medium (DMEM) containing 10% fetal bovine serum (FBS), 100 U/mL penicillin-G and 100 µg/mL streptomycin.

The cellular uptake of localization of 1 in HCT-116 tumor cells was then evaluated using fluorescence microscopy. Fortunately, spirohexenolide A (1) was natively fluorescent, with an excitation maximum $\lambda_{max}$=435 nm and emission maximum at $\lambda_{max}$=466 nm. HCT-116 cells were treated with 10 µM 1 in DMEM containing 10% FCS, 100 U/mL penicillin-G and 100 µg/mL streptomycin and analyzed by fluorescence microscopy. As shown in FIGS. 6a-6b, spirohexenolide A (1) localized with punctuate distribution in a subcellular organelle between the Golgi apparatus and the nucleus, such as the ER-Golgi intermediate compartment. The localization of 1 was confirmed by counterstaining with BODIPY-FL brefeldin A (Invitrogen™). This effect was not due to aberrant effects from the media as changing from DMEM to McCoys' 5A (McCoy's 5A with 1.5 mM glutamine, 10% FBS, 0.025 mM HEPES, 100 U/mL penicillin-G and 100 µg/mL), removal of the antibiotics, and elimination of phenol red.

The effects of 1 on the cell cycle were also evaluated. HCT-116 cells cultured in DMEM were treated 1 h before the onset of mitosis with 10 µM 1 in DMEM. After 12 h (several hours after the completion of mitosis), the cells were fixed for 5 min with 0.5% formalin and 0.1% glutaraldehyde in PBS pH 7.2, washed extensively with PBS pH 7.2, treated with a cocktail of fluorescent probes to visualize DNA, actin, and microtubules and examined using three-color confocal fluorescence microscopy. Compound 1 induced cell cycle arrest during mitosis leaving a common phenotype (FIG. 6a) that could be characterized by an incomplete segregation of the cells and an apparent failure to complete entry into cytokinesis (FIG. 6c). Inhibition at this stage in mitosis coupled with cellular localization indicated a unique mode of action and merits further investigation.

A new spirotetronate polyketide, spirohexenolide A (1), has been identified and isolated from *S. platensis*. Its structure has been elucidated through spectroscopic and X-ray crystallographic analyses. The evidence provided herein shows that mutagenesis can be used to encourage production of otherwise silent natural product pathways (Bode et al., ChemBio-Chem, 3:619-627 (2002)). Activity analyses indicated that 1 displayed potent activity against tumor cell growth with a unique specificity to select tumor cell lines (cf. NCI-C60 screening data in the Supporting Information). The combination of the unique structure and activity of 1 serves as the starting point for the development both chemical synthesis and mechanism of action studies.

Example 3

Targeting of Spirohexenolide to Human Migration Inhibitory Factor (hMIF) Protein EXAMPLES 1 and 2 describe the identification of two novel bioactive spirotetronates, spirohexenolide A (1) and B (2) from the application of mutagenesis and clonal selection techniques to strains of *Streptomyces platensis* (Kang 2009). The structure of 1 and 2 were elucidated through X-ray crystallography indicating a unique carbon skeleton composed of four fused rings that harbor a polyunsaturated spirotetronate. NCI-60 screening of 1 indicated that while active in a number of tumor cell lines, COMPARE analyses indicated mode of action (MOA) of 1 did not match that of established classes of antitumor agents. This was further confirmed by evaluating the uptake and localization of spirohexenolide A (1) in live tumor cells. With this data in hand, the focus turned toward labeling the 8-hydroxylgroup R=OH in compound 1.

The first step was adding a tag by esterification. Conventional conditions such as that of the Keck-modified Steiglichesterification (DCC, DMAP, CSA), Mukaiyamaesterification (2-chloro-1-methylpyridinium iodide), Mitsunobu reaction (PPh$_3$, DEAD) returned only unlabeled 1 using a panel of immunoaffinity fluorescent (IAF) labels (Alexander 2006).

The next focus was the stepwise process wherein the linker and IAF label are installed in two steps. First, 1 was acylated with 4-azidobutanoylchloride to afford corresponding azide and then installing the IAF label by aHüisgencycloaddition. This approach provided probe 3 from 1. Samples of probe 3 were then screened for activity using the MTT assay in HCT-116 cells returning an activity that was significantly less active than 1.

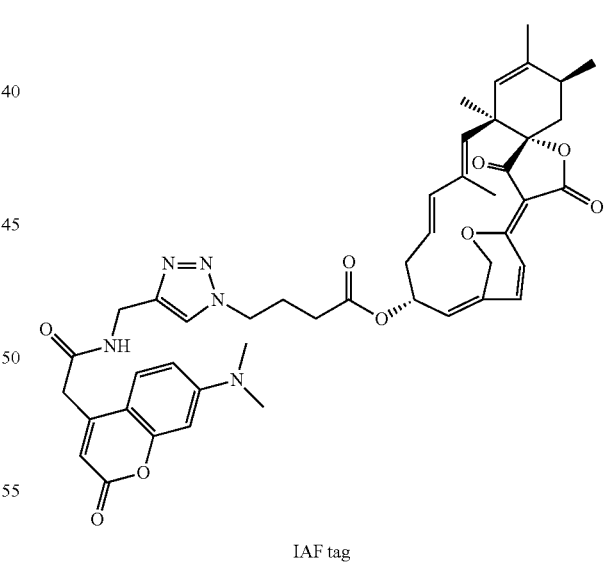

IAF tag

To minimize any loss in activing with probe 3, a second approach was examined. Addition of 1 to an excess of succinylchloride in CH$_2$Cl$_2$ afforded a mixture of chromatographically separable di- and mono-functional succinates, which through slow addition could be directed to provide the monoadduct. The resulting acid was then coupled to IAF amine tag to afford probe 4 from 1. Samples of probe 4 were then screened for activity using the MTT assay in HCT-116 cells returning an activity that was slightly less active than 1.

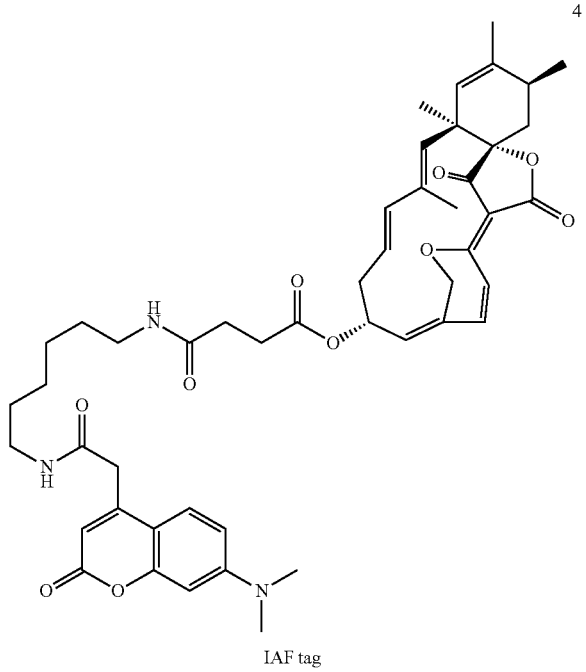 [SMILES: CC1=C[C@]2(C)/C=C(C)/C=C/C[C@@H](OC(=O)CCC(=O)NCCCCCCNC(=O)Cc3cc(=O)oc4cc(N(C)C)ccc34)/C=C3C=C/C(=C4\C(=O)O[C@]2(C[C@@H]1C)C4=O)OC/3]

IAF tag

These studies indicate that while the probes 3 and 4 were less active than the parent natural product, the processing of probe 4 in live cells matches that of the parent natural product. We recently demonstrated that two-color imaging methods can be used not only to extend the quality of imaging but also confirmed the stability of the probe in live cells. While slightly less active, we have demonstrated the preparation of active analogs of 1 and are in the process of applying the affinity features of the IAF tag to screen HCT-116 cell lysates for the biomolecular targets.

Figure 8:
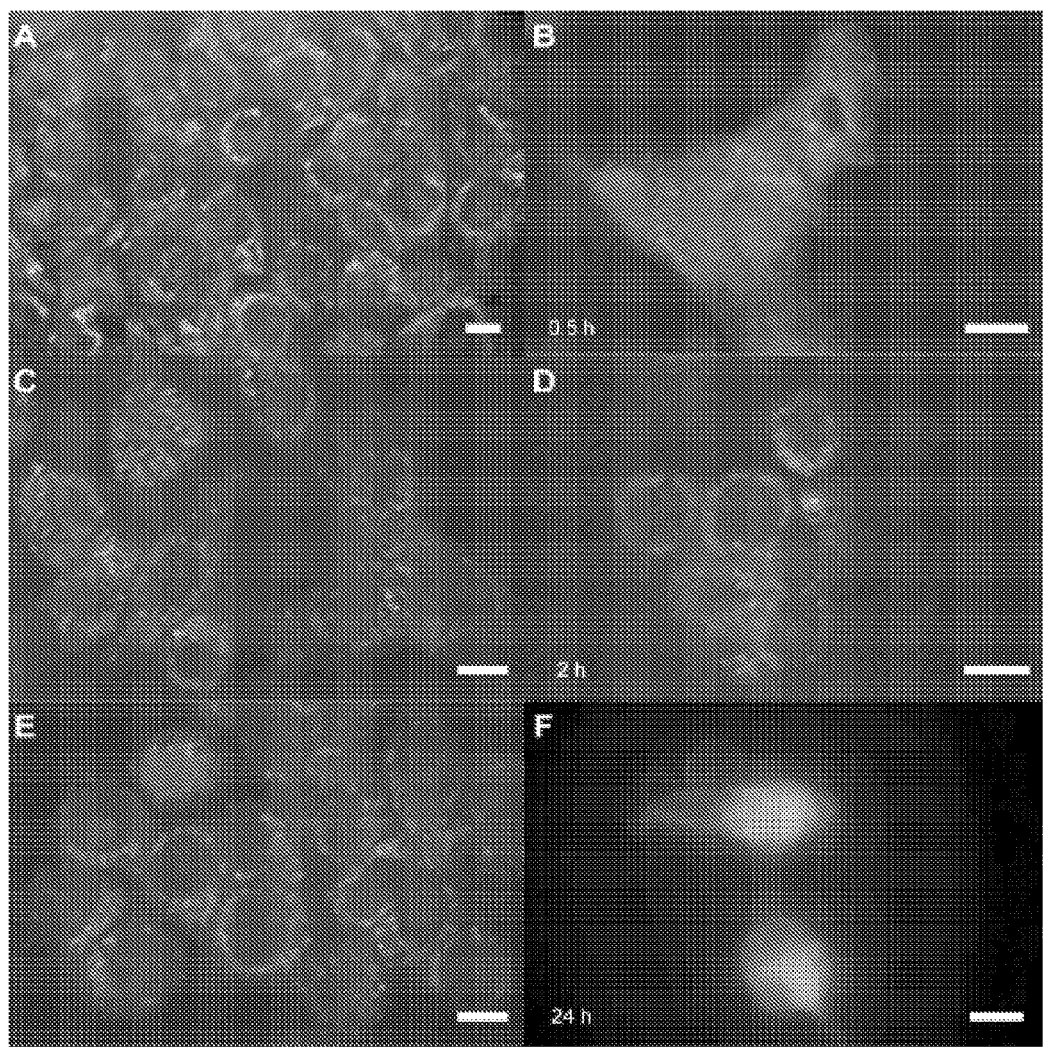
FIG. 8 shows confocal fluorescent images depicting HCT-116 cells treated for 6 h with A) 10 µM spirohexenolide A (1), B) 10 µM probe 2 or C) 10 µM probe 3. Comparable subcellular localization was observed. Cells were treated for 6 h, washed twice with media and imaged live. D-F) Frames from a time lapse imaging study depicting the movement of probe 3 in live HCT-116 cells over 24 h. Cells were treated at time=0 with 10 µM probe 3. Bars indicate 10 µm.

The uptake and subcellular localization of probes 3 and 4 to spirohexenolide A (1) in HCT-116 cells were then compared. Fortunately, spirohexenolide A (1) was natively fluorescent, with an excitation maximum λmax=435 nm and emission maximum at λmax=466 nm. HCT-116 cells were treated with 10 μM 1 in DMEM containing 10% FCS, 100 U/mL penicillin-G, and 100 μg/mL streptomycin and analyzed by fluorescence microscopy. Spirohexenolide A (1) was readily uptaken and appeared within minutes throughout the cell (FIG. 8a). Within 6-12 hours, fluorescence from 1 concentrated within vesicles surrounding the nucleus and remained in these structures. This staining could not be washed from the cells by repetitive incubation with media and remained consistent thereafter. Co-staining experiments with a panel of organelle probes provided a direct correlation with LysoTracker Red DND-99 indicating that the localization occurred in the lysosomes. While probe 2 as not failed to provide an identical localization (FIG. 8B), probe 4 underwent comparable subcellular localization as shown in FIG. 8C. Time course studies were conducted to denote the movement of probe 4 over time as shown in FIGS. 8D-8F. Cells treated probe 3, as well as the parent natural product 1, returned cells that displayed the characteristic apoptotic phenotype as shown in FIG. 8F.

These studies indicate that while probes 3 and 4 were less active in our cell screens, probe 4 was uptaken and processed in a similar manner to 1 in HCT-116 cells, as processing of probe 4 in live cells matched that of the parent natural product. We demonstrated that two-color imaging methods can be used not only to extend the quality of imaging but also confirmed the stability of the probe in live cells. While slightly less active, we have demonstrated the preparation of active analogs of 1 and are in the process of applying the affinity features of the IAF tag to screen HCT-116 cell lysates for the biomolecular targets.

Figure 9:
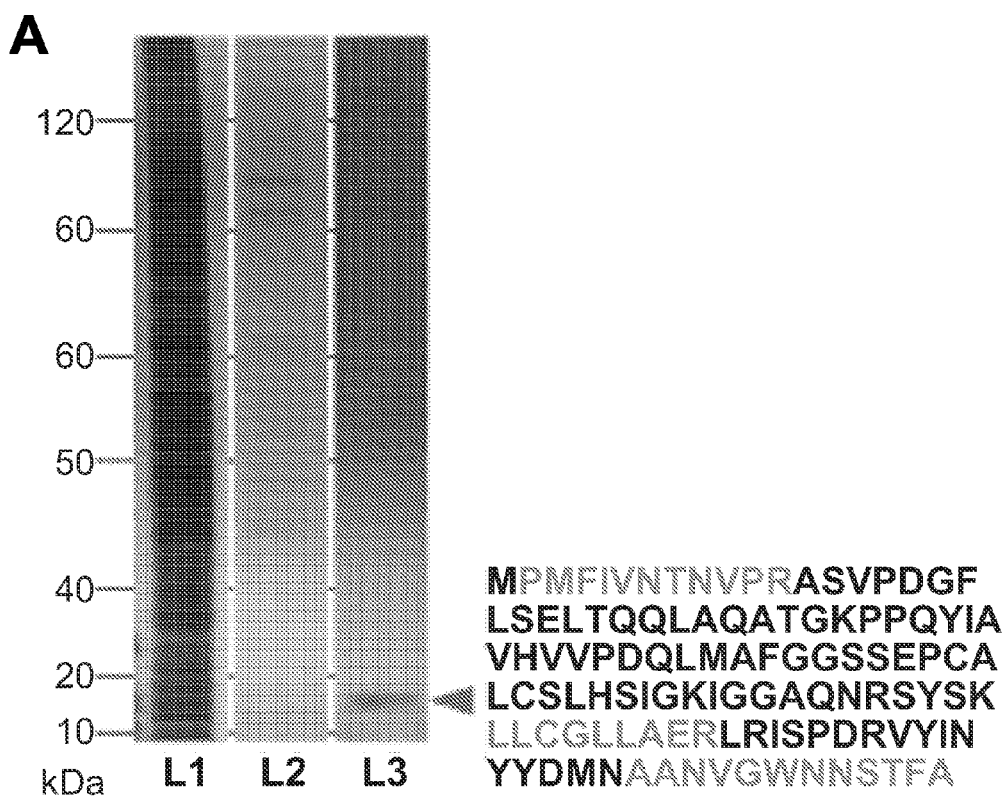
FIG. 9 shows the identification of human migration inhibitory factor (hMIF) as a target of the spirohexenolides. A) Anti-IAF immunoprecipitation studies identify a ~12 kDa band. Lane L1, L2 and L3 depict HCT116 cell lysate, an IAF dye elution (bands correspond to fragments of the anti-IAF mAb) and glycine wash, respectively. The ~12 kDa band was identified in the glycine wash. B) Trypsin-digest LC-MS/MS analysis identified three peptides that overlapped with the hMIF protein (shown in red). C) Western blot analysis using a mouse anti-MIF mAb confirmed the presence of hMIF in the immunoprecipitated fraction of HCT-116 cell lysate, as well as in *E. coli* lysates bearing recombinant hMIF. Arrow denotes the position of hMIF. The upper bands arose from the mouse anti-IAF mAb used in this experiment (background).
Figure 9:
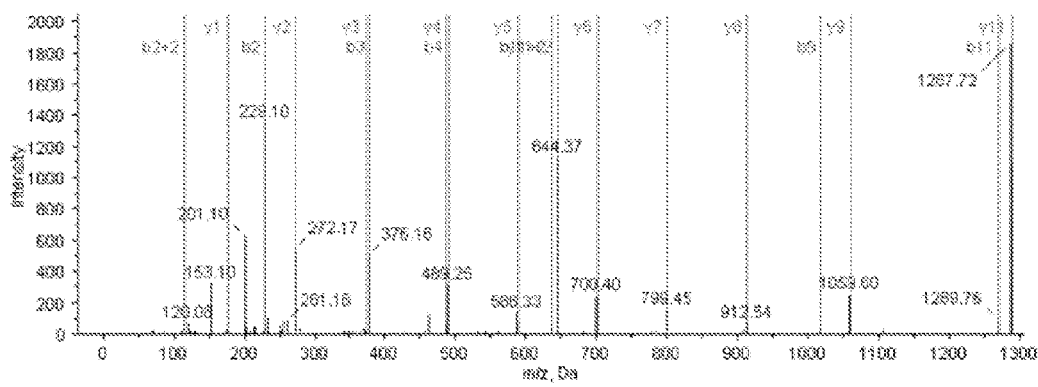
Figure 9:
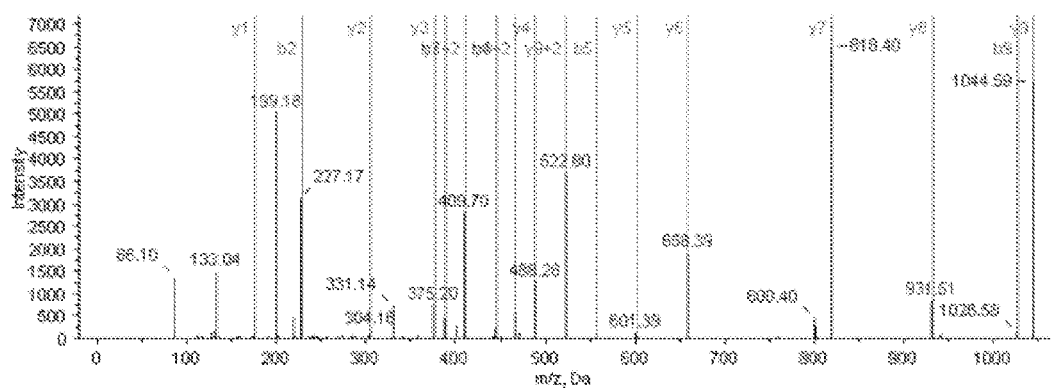
Figure 9:
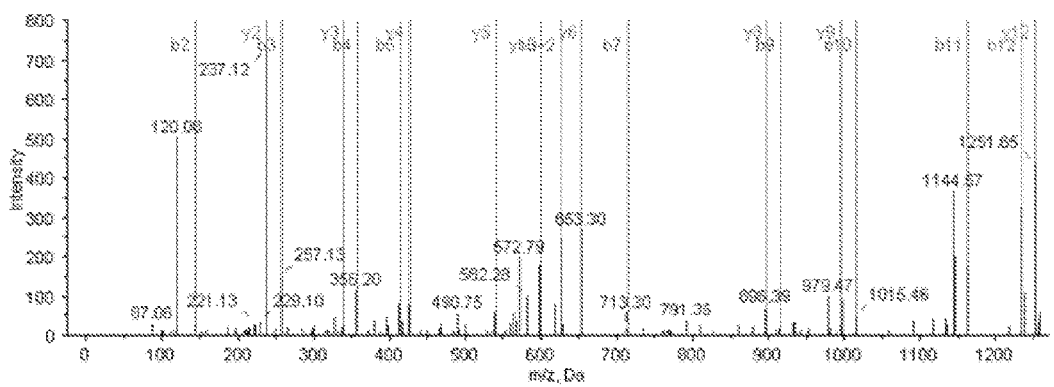
Figure 9:
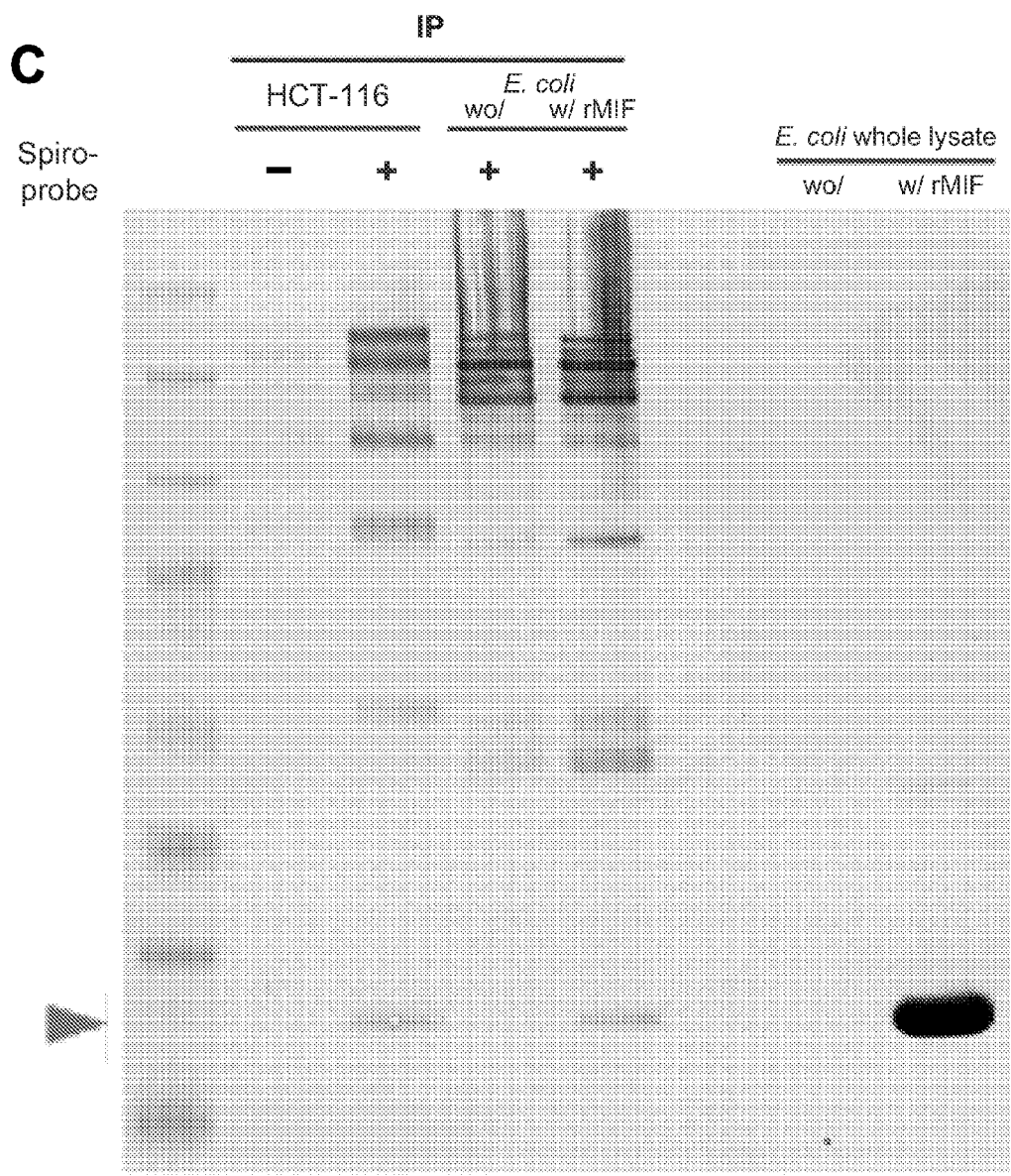
Figure 10:
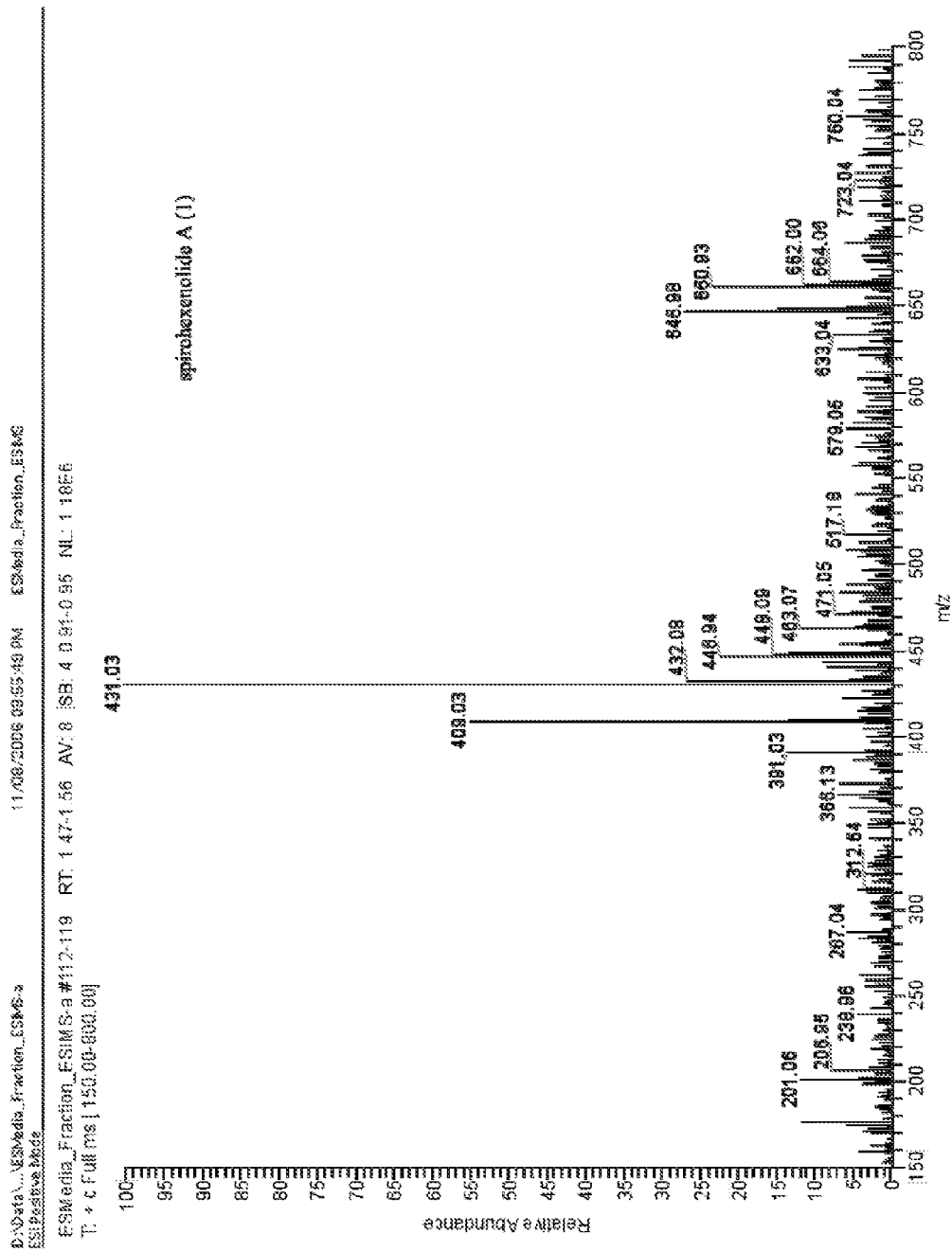
FIGS. 10-11 shows the mass spectrum for spirohexenolide A(1).
Figure 11:
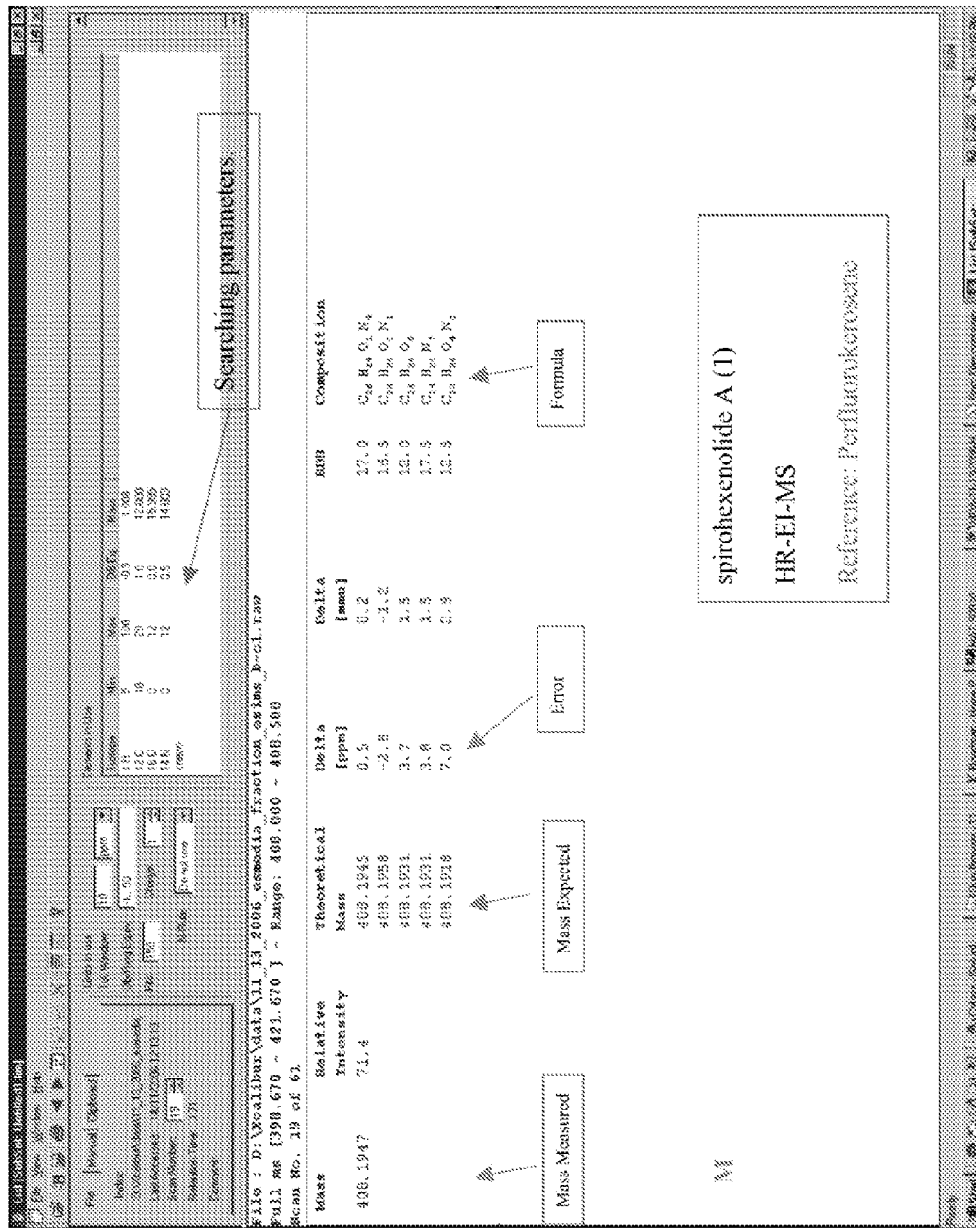
Figure 12:
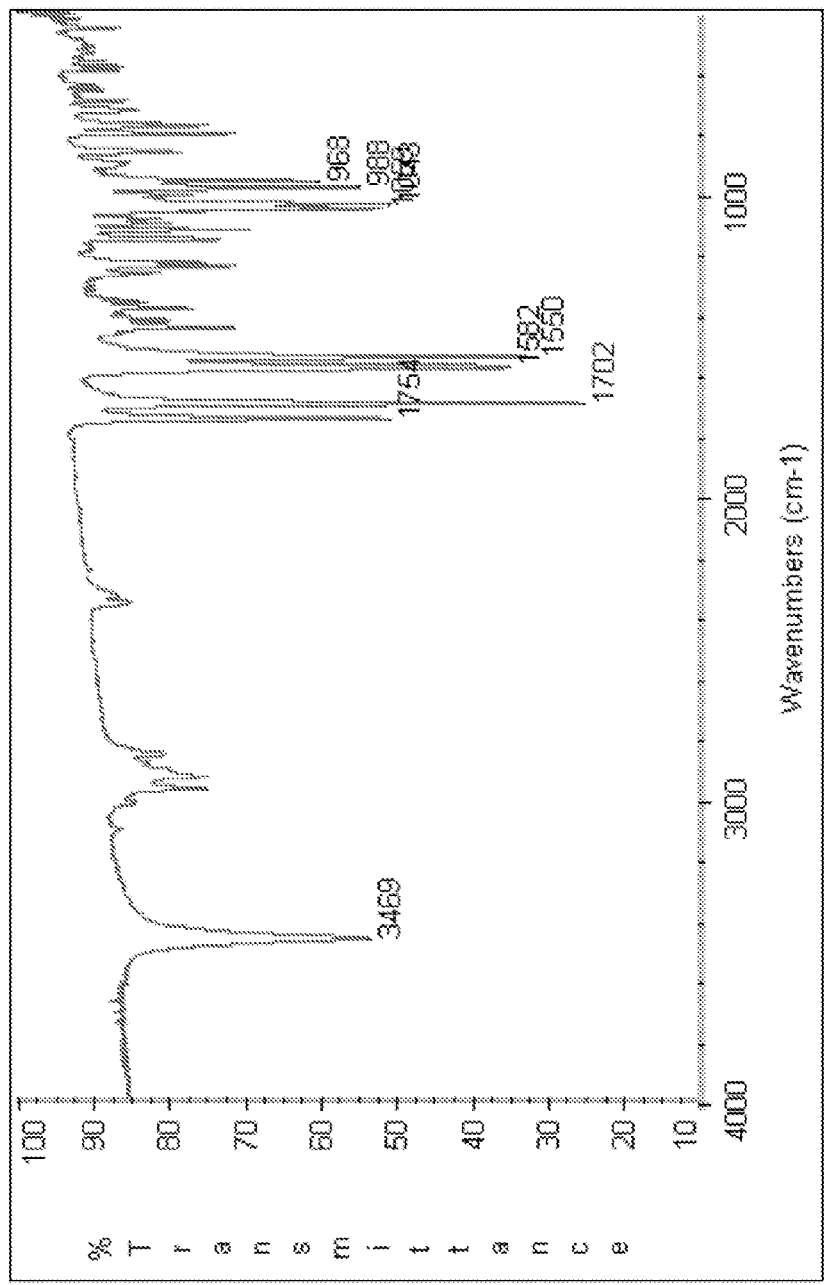
FIG. 12 shows the FT-IR spectrum for spirohexenolide A(1).
Figure 13:
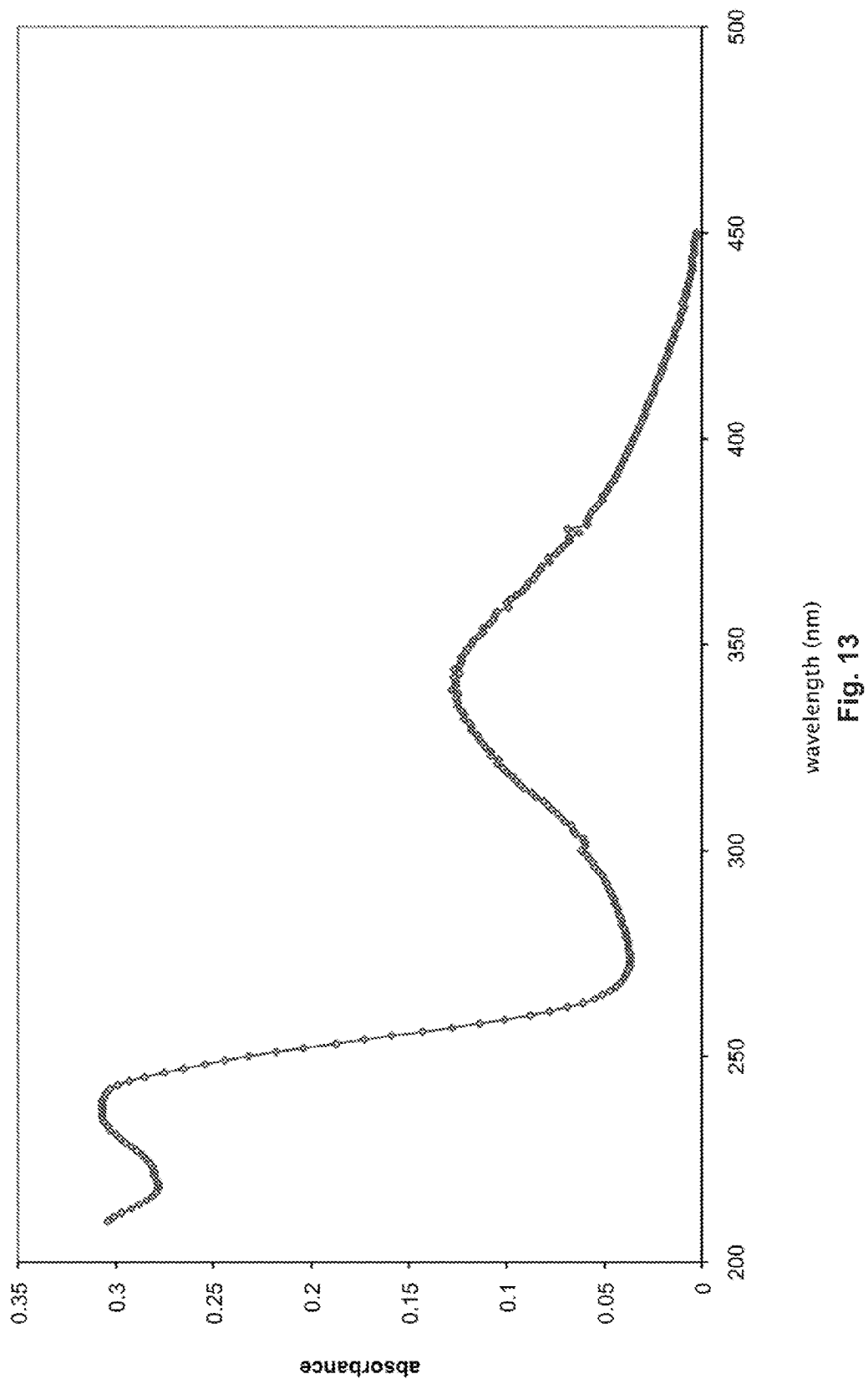
FIG. 13 shows the absorbance spectrum for spirohexenolide A(1).

Attention was then turned to screening for proteins that bind to the spirohexenolides. Using the affinity properties of the IAF probe 4, we deployed an anti-IAF tag immunoprecipitation protocol to isolate a 12 kDa band (Lane L3 in FIG. 9A). Trypsin-digest LC-MS/MS protein identification studies returned three peptides (FIG. 9B) that appeared within the human migration inhibitory factor (hMIF) as shown by highlighting in FIG. 9A. Western blot analysis (FIG. 9C) confirmed hMIF the identification of hMIF.

All publications and patent applications cited in this specification are herein incorporated by reference in their entirety for all purposes as if each individual publication or patent application were specifically and individually indicated to be incorporated by reference for all purposes.

Although the foregoing methods and compositions have been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

What is claimed:

1. A compound of formula (III) or a pharmaceutically acceptable salt thereof:

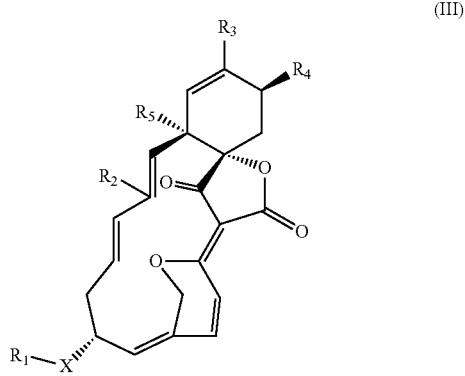

(III)

wherein X is a —O—C(=O)—;
$R_1$ is H, $C_1$-$C_6$ alkyl, $C_2$-$C_6$ alkenyl, $C_2$-$C_6$ alkynyl, $C_1$-$C_6$ alkoxy, —$CF_3$, aryl, heteroaryl, or a label;
or X—$R_1$ is —H or —OH; and
$R_2$, $R_3$, $R_4$, and $R_5$ are —$CH_3$.

2. The compound of claim 1, wherein the compound has the structure and stereochemical configuration of formula (VII):

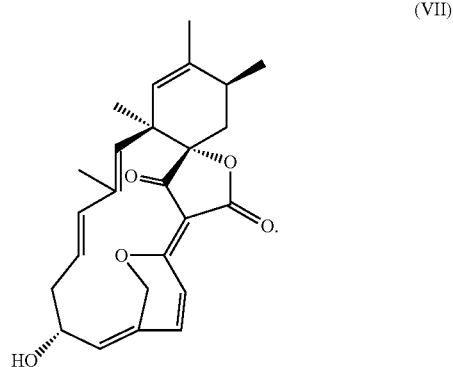 [SMILES: CC1=C[C@]2(C)/C=C(C)/C=C/C[C@@H](O)/C=C3C=C/C(=C4\C(=O)O[C@]2(C[C@@H]1C)C4=O)OC/3]

(VII)

3. The compound of claim 1, wherein the compound has the structure and stereochemical configuration of formula (VIII):

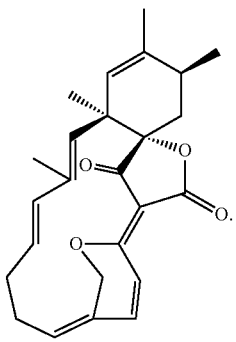

(VIII)

4. The compound of claim 1, wherein $R_1$ is a label.

5. The compound of claim 4, wherein the label is an immunological label, fluorescent label, a chemiluminescent label, a radioisotope label, an enzyme label, a particulate label, a colorimetric label, or an energy transfer agent.

6. The compound of claim 4, wherein the label is α-methoxy-α-trifluoromethylphenylacetic acid (MTPA), fluorescent dye, affinity tag, soublizing group, or an immunoaffinity fluorescent (IAF) label.

7. A method of screening for proteins that bind to the compound of claim 1, comprising exposing a cancerous tissue to a compound comprising a label and detecting the presence of the labeled compound.

8. A process for preparing a compound having a formula of:

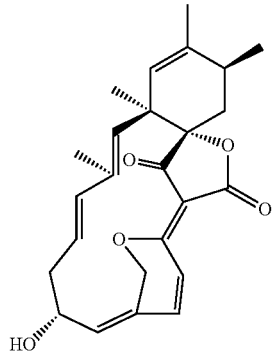

-continued
or

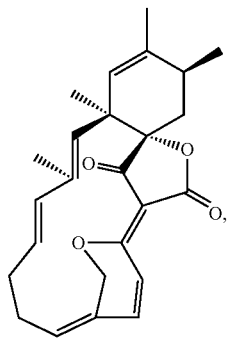

the method comprising culturing a microorganism having the identifying characteristics of *Streptomyces platensis* under suitable conditions, allowing the compound to accumulate in the culture medium, and isolating the compound from the culture medium.

9. The process of claim 8, further comprising the steps of:

inducing mutations in *Streptomyces platensis* microorganisms by exposing the microorganisms to a mutagen;

selecting the resulting microorganisms having a desired trait; and culturing the selected organisms.

10. The process of claim 9, wherein the mutagen is ultraviolet irradiation, ionizing radiation, or a chemical mutagen.

11. The process of claim 9, wherein the desired characteristic is decreased contact inhibition.

12. The process of claim 8, wherein the microorganism is strain MJ1A1 or MJ1A2 of *Streptomyces platensis*.

13. A pharmaceutical composition comprising a therapeutically effective amount of a compound of claim 1 and a pharmaceutically acceptable excipient.

14. The pharmaceutical composition of claim 13, wherein the compound of claim 1 is the compound of claim 2.

15. The pharmaceutical composition of claim 13, wherein the compound of claim 1 is the compound of claim 3.

* * * * *